United States Patent
Van Camp et al.

(10) Patent No.: US 6,900,244 B2
(45) Date of Patent: May 31, 2005

(54) ANILINO LIVER X-RECEPTOR MODULATORS

(75) Inventors: Jennifer Ann Van Camp, Glencoe, IL (US); James W. Malecha, Libertyville, IL (US); Julie M. Miyashiro, Skokie, IL (US); Gary A. DeCrescenzo, St. Charles, MO (US); Joe T. Collins, Ballwin, MO (US); Monica J. Kalman, Skokie, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/444,349

(22) Filed: May 23, 2003

(65) Prior Publication Data

US 2004/0087632 A1 May 6, 2004

Related U.S. Application Data

(60) Provisional application No. 60/383,078, filed on May 24, 2002.

(51) Int. Cl.[7] .................. C07C 229/40; C07C 237/20; A61K 31/195; A61K 31/165
(52) U.S. Cl. ............... 514/538; 514/567; 514/670; 514/646; 548/558; 544/164; 560/45; 562/456; 564/170; 564/305; 564/355
(58) Field of Search .................. 562/456; 560/45; 564/170, 305, 355; 514/538, 567, 620, 646; 548/558; 544/164

(56) References Cited

U.S. PATENT DOCUMENTS

| | | | |
|---|---|---|---|
| 4,267,193 A | 5/1981 | Neustadt et al. |
| 4,322,434 A | 3/1982 | Neustadt et al. |
| 5,011,851 A | 4/1991 | Meanwell |
| 5,639,616 A | 6/1997 | Liao et al. |
| 6,316,503 B1 | 11/2001 | Li et al. |
| RE37,770 E | 6/2002 | Elias et al. |
| 2001/0018428 A1 | 8/2001 | Zablocki et al. |
| 2001/0020030 A1 | 9/2001 | Stewart et al. |
| 2002/0013334 A1 | 1/2002 | Robl et al. |
| 2002/0016364 A1 | 2/2002 | Luchoomun et al. |
| 2002/0037872 A1 | 3/2002 | Palle et al. |
| 2002/0045607 A1 | 4/2002 | Beachy et al. |
| 2002/0048572 A1 | 4/2002 | Shan et al. |
| 2002/0120137 A1 | 8/2002 | Houze et al. |
| 2002/0165394 A1 | 11/2002 | Dumas et al. |

FOREIGN PATENT DOCUMENTS

| | | |
|---|---|---|
| EP | 0 135 894 A2 | 4/1985 |
| EP | 0 558 062 A2 | 9/1993 |
| WO | WO 91/00277 | 1/1991 |
| WO | WO 91/00281 | 1/1991 |
| WO | WO 96/19493 | 6/1996 |
| WO | WO 96/34851 | 11/1996 |
| WO | WO 99/19300 | 4/1999 |
| WO | WO 00/54759 | 9/2000 |
| WO | WO 00/55118 | 9/2000 |
| WO | WO 00/56710 | 9/2000 |
| WO | WO 01/60818 A1 | 8/2001 |
| WO | WO 02/20463 A2 | 3/2002 |
| WO | WO 02/24632 A2 | 3/2002 |
| WO | WO 02/46141 A2 | 6/2002 |
| WO | WO 02/46172 A2 | 6/2002 |
| WO | WO 02/46181 A2 | 6/2002 |
| WO | WO 02/058690 A2 | 8/2002 |

OTHER PUBLICATIONS

Cas Registry No. 329915–55–1.
Chkanikov et al., "Hexafluoroacetone and Methyl Trifluoropyruvate as Precursors of Modified Esters of N–Acyl–N–Phenyl or Amino Acids"; 1993, pp. 1415–1424, Plenum Publishing Corporation.
International Search Report, PCT/US 03/16382; 6 sheets.
Chkanikov, et al., "Hexafluoroacetone and Methyl Trifluoropyruvate as Precursors of Modified Esters of N–acyl–N–phenyl–.alpha.–amino acids" Cas Registry No. 147749–06–2 (Database Accession No. 118:255272 XP002253208).
International Preliminary Examination Report, dated Mar. 30, 2004 (5 pages).

*Primary Examiner*—Bernard Dentz
(74) *Attorney, Agent, or Firm*—Peter C. Richardson; Gregg C. Benson; Lisa A. Samuels

(57) ABSTRACT

The present invention is directed to selective LXR modulators, small molecule compounds corresponding to Formula I and is further directed to a process of treating a condition in a mammal that is modulated by LXR using a therapeutically effective dose of a compound of Formula I.

14 Claims, No Drawings

ANILINO LIVER X-RECEPTOR MODULATORS

REFERENCE TO RELATED APPLICATIONS

This application claims the benefit of U.S. provisional application Ser. No. 60/383,078, filed May 24, 2002, the entire disclosure of which is herein incorporated by reference.

BACKGROUND

Liver X-receptors (LXRs) are nuclear receptors that regulate the metabolism of several important lipids, including cholesterol and bile acids. Most of the cholesterol in plasma is transported on three major lipoprotein classes; VLDL cholesterol (VLDL-C), LDL cholesterol (LDL-C) and HDL cholesterol (HDL-C). Total cholesterol is the sum of all three lipoproteins. Both VLDL-C and LDL-C are associated with atherogenic processes while HDL-C is believed to facilitate cholesterol removal from tissues (e.g. atherosclerotic plaques) and thus have a protective effect on coronary heart disease.

LXR represents a novel intervention point to regulate the reverse cholesterol transport (RCT) pathway, i.e., the removal of cholesterol from peripheral tissues/cells and subsequent uptake via the liver for disposal. Removal of cellular cholesterol requires active transport of free cholesterol across the plasma membrane and onto HDL particles. This transfer of cholesterol from inside the cell and onto HDL in the plasma is mediated by ATP binding cassette 1 (ABCA1) transporter protein. The observation that LXR is a key transcriptional activator of ABCA1 in the macrophage, suggests that induction of LXR will lead to an increase in cholesterol efflux from the macrophage. In addition, it is known that LXR regulates the induction of other genes involved in RCT such as apoE and cholesterol ester transport protein (CETP), suggesting that activating the LXR pathway should also lead to increased uptake of cholesterol by the liver. Thus, activation of LXR by a small molecule ligand will lead to an up-regulation of ABCA1 and induction of the reverse cholesterol transport pathway thereby increasing cholesterol efflux to HDL-C and reducing the cholesterol content of atherosclerotic plaques.

SUMMARY OF THE INVENTION

In general, the present invention is directed to LXR modulators being small-molecule compounds corresponding to Formula (I) and the isomers, tautomers, salts and prodrugs thereof:

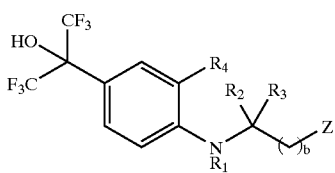

(Formula I)

wherein:
b is 0–3;
$R_1$ is hydrogen, or optionally substituted alkyl, heterocyclo, or aralkyl;
$R_2$ and $R_3$ are independently hydrogen or optionally substituted alkyl, aryl, heteroaryl, aminoalkyl, hydroxyalkyl, or thioalkyl; one of $R_2$ and $R_3$ together with $R_1$ and the atoms to which they are attached may form a heterocyclic ring, or $R_2$ and $R_3$ together with the atom to which they are attached may form a carbocyclic or heterocyclic ring;
$R_4$ is hydrogen or together with $R_1$ and the atoms to which they are attached form a heterocyclic ring;
Z is —$CO_2Z_1$, —$CH_2NZ_1Z_2$, —$C(O)Z_1$, —$CH(OH)Z_1$, —$CH_2OZ_1$, —$CH_2OC(O)Z_1$, or —$C(O)NZ_1Z_2$, and
$Z_1$ and $Z_2$ are independently hydrogen or optionally substituted alkyl, heterocyclo, or aralkyl;
provided, however, when $R_1$ is hydrogen and one of $R_2$ and $R_3$ is hydrogen, the other of $R_2$ and $R_3$ is not hydrogen or methyl.

Other objects of the invention will be in part apparent and in part pointed out hereinafter.

DETAILED DESCRIPTION OF THE PREFERRED EMBODIMENTS

In general, the present invention is directed to small molecule compounds corresponding to Formula (I) and each of the other formulae disclosed herein, the isomers, tautomers, salts and prodrugs thereof and their use as LXR modulators. In particular, the LXR modulators may be used in the treatment of atherosclerosis, dyslipidemia, diabetes, Alzheimers disease or Niemann-Pick disease.

In general, $R_1$ is hydrogen or optionally substituted alkyl, heterocyclo, or aralkyl. In one embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In another embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, amino, aryl and heteroaryl. For example, $R_1$ may be hydrogen, methyl, substituted methyl (e.g., trifluoromethyl), ethyl, substituted ethyl (e.g., trifluoroethyl and 2-methoxyethyl), propyl and the like; in one such embodiment, $R_1$ is methyl, ethyl, trifluoromethyl, trifluoroethyl or 2-methoxyethyl. Alternatively, $R_1$ may be optionally substituted cycloalkyl; for example, $R_1$ may be cyclopropyl, cyclobutyl, cyclopentyl, etc., optionally substituted with any of the aforementioned substituents. Alternatively, $R_1$ may be benzyl or other aralkyl optionally substituted with halogen, hydroxy, alkoxy and the like; for example, $R_1$ may be benzyl, 4-methylbenzyl, 4-ethoxybenzyl, 4-methoxybenzyl, 4-halobenzyl, 2-halobenzyl, 3,4-dihalobenzyl and the like. Alternatively, $R_1$ together with $R_4$ and the atoms to which they are attached may form a fused ring (with the ring to which $R_4$ is shown as being bonded in Formula 1); for example, $R_1$ together with $R_4$ and the atoms to which they are attached may form a fused ring. Alternatively, $R_1$ together with one of $R_2$ and $R_3$ the atoms to which they are attached may form a heterocyclic ring; for example, $R_1$ together with one of $R_2$ and $R_3$ and the atoms to which they are attached may form an optionally substituted pyrrolidine or piperidine ring.

In one embodiment, Z is —$CO_2Z_1$, —$CH_2NZ_1Z_2$, —$C(O)Z_1$, —$CH(OH)Z_1$, —$CH_2OZ_1$, —$CH_2OC(O)Z_1$, or —$C(O)NZ_1Z_2$, and $Z_1$ and $Z_2$ are independently hydrogen, or optionally substituted alkyl, heterocyclo, or aralkyl. In one embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In another embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, amino, aryl and heteroaryl. For example, in one embodiment, Z is —$CO_2Z_1$ and $Z_1$ is methyl, ethyl or other lower alkyl; in each of these embodiments the alkyl group may optionally be substituted with one or more of the aforementioned substituents. Alternatively, Z may be —$CH_2NZ_1Z_2$ wherein $Z_1$ and $Z_1$ are independently hydrogen, methyl, ethyl or other lower alkyl, methoxy or other lower alkoxy, benzyl, substituted benzyl and the like. Alternatively, Z may be —$C(O)Z_1$ wherein $Z_1$ is methyl, ethyl, propyl or other lower alkyl; in each of these embodiments the alkyl group may optionally be substituted with one or more of the aforementioned substituents. Alternatively, Z is —$CH(OH)Z_1$ wherein $Z_1$ is hydrogen, methyl, ethyl, propyl or other lower alkyl; in each of these embodiments the alkyl group may optionally be substituted with one or more of the aforementioned substituents. Alternatively, Z is —$CH_2OZ_1$ wherein $Z_1$ is methyl, ethyl, propyl or other lower alkyl; in each of these embodiments the alkyl group may optionally be substituted with one or more of the aforementioned substituents. Alternatively, Z is —$CH_2OC(O)Z_1$ wherein $Z_1$ is methyl, ethyl, propyl or other lower alkyl; in each of these embodiments the alkyl group may optionally be substituted with one or more of the aforementioned substituents. Alternatively, Z is —$C(O)NZ_1Z_2$ wherein $Z_1$ and $Z_1$ are independently hydrogen, methyl, ethyl or other lower alkyl, methoxy or other lower alkoxy, benzyl, substituted benzyl and the like.

In a further embodiment of the present invention, the LXR modulators correspond to Formula I wherein $R_4$ is hydrogen and $R_2$ and $R_3$ together with the atoms to which they are attached to form an optionally substituted ring. In this embodiment for example, the compounds correspond to Formula II;

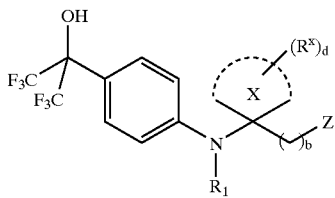

(Formula II)

wherein:
the ring denoted as X is a carbocyclic or heterocyclic ring;
each $R^x$ is independently hydrogen, hydroxy, halo, lower alkyl, alkoxy, cyano, nitro or alkylthio;
d is 0–3; and
b, $R_1$, and Z are as defined in connection with Formula I.

In one such embodiment in which the LXR modulators correspond to Formula II, the X ring may define a 3–6, more typically a 5–6 member carbocyclic or heterocyclic ring. For example, the X ring may be a cyclopentyl or cyclohexyl ring; alternatively, the X ring may be a tetrahydro-2H-pyran-4-yl, 1,1-dioxytetrahydro-2H-thiopyran-4-yl, or N-benzylpiperidine-4-ylpiperidinyl ring. In each of these embodiments, the X ring may optionally be substituted by one or more substituents (i.e., when d>0 and $R^x$ is other than hydrogen) selected, for example, from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In addition, when d is at least two and $R^x$ is other than hydrogen, two of the $R^x$ substituents may combine to form a fused ring (e.g., wherein the two $R^x$ substituents define a fused ring comprising a methylene dioxy or ethylene dioxy linkage).

In one such embodiment in which the LXR modulators correspond to Formula II, $R_1$ is hydrogen, or an optionally substituted alkyl, or aralkyl. In this embodiment, for example, $R_1$ may be hydrogen, acyl, or optionally substituted alkyl, heterocyclo, or aralkyl. In one embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In another embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, amino, aryl and heteroaryl. For example, $R_1$ may be hydrogen, methyl, substituted methyl (e.g., trifluoromethyl), ethyl, substituted ethyl (e.g., trifluoroethyl and 2-methoxyethyl), propyl and the like; in one such embodiment, $R_1$ is methyl, ethyl, trifluoromethyl, trifluoroethyl or 2-methoxyethyl. Alternatively, $R_1$ may be optionally substituted cycloalkyl; for example, $R_1$ may be cyclopropyl, cyclobutyl, cyclopentyl, etc., optionally substituted with any of the aforementioned substituents. Alternatively, $R_1$ may be benzyl or other aralkyl optionally substituted with halogen, hydroxy, alkoxy and the like; for example, $R_1$ may be benzyl, 4-methylbenzyl, 4-ethoxybenzyl, 4-methoxybenzyl, 4-halobenzyl, 2-halobenzyl, 3,4-dihalobenzyl and the like. Alternatively, $R_1$ together with $R_4$ and the atoms to which they are attached may form a fused ring (with the ring to which $R_4$ is shown as being bonded in Formula 1); for example, $R_1$ together with $R_4$ and the atoms to which they are attached may form a fused ring. In addition, in each of these alternative embodiments, the X ring may define a 3–6, more typically a 5–6 member carbocyclic or heterocyclic ring as previously described.

In one such embodiment in which the LXR modulators correspond to Formula II, Z is —$CO_2Z_1$, —$CH_2NZ_1Z_2$, —$C(O)Z_1$, —$CH(OH)Z_1$, —$CH_2OZ_1$, —$CH_2OC(O)Z_1$, or —$C(O)NZ_1Z_2$, and $Z_1$ and $Z_2$ are independently hydrogen, or optionally substituted alkyl, heterocyclo, or aralkyl. In one embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In another embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, amino, aryl and heteroaryl. For example, in one embodiment, Z is —$CO_2Z_1$ and $Z_1$ is methyl, ethyl or other lower alkyl; in each of these embodiments the alkyl group may optionally be substituted with one or more of the aforementioned substituents. Alternatively, Z may be —$CH_2NZ_1Z_2$ wherein $Z_1$ and $Z_1$ are independently hydrogen, methyl, ethyl or other lower alkyl, methoxy or other lower alkoxy, benzyl, substituted benzyl and the like. Alternatively, Z may be —$C(O)Z_1$ wherein $Z_1$ is methyl, ethyl, propyl or other lower alkyl; in each of these embodiments the alkyl group may optionally be substituted with one or more of the aforementioned substituents. Alternatively, Z is —$CH(OH)Z_1$ wherein $Z_1$ is hydrogen, methyl, ethyl, propyl or other lower alkyl; in each of these embodiments the alkyl group may optionally be substituted with one or more of the aforementioned substituents. Alternatively, Z is —$CH_2OZ_1$ wherein $Z_1$ is methyl, ethyl, propyl or other lower alkyl; in each of these embodiments the alkyl group may optionally be substituted with one or more of the aforementioned substituents. Alternatively, Z is —$CH_2OC(O)Z_1$ wherein $Z_1$ is methyl, ethyl, propyl or other lower alkyl; in each of these embodiments the alkyl group may optionally be substituted with one or more of the aforementioned substituents. Alternatively, Z is —$C(O)NZ_1Z_2$ wherein $Z_1$ and $Z_1$ are independently hydrogen, methyl, ethyl or other lower alkyl, methoxy or other lower alkoxy, benzyl, substituted benzyl and the like. In addition, in each of these alternative embodiments, the X ring may define a 3–6, more typically a 5–6 member carbocyclic or heterocyclic ring as previously described.

In a further embodiment, the LXR modulators correspond to Formula I wherein $R_4$ is hydrogen and $R_1$ together with one of $R_2$ and $R_3$ and the atoms to which they are attached to form a heterocyclic ring. In this embodiment, the compounds correspond to Formula III:

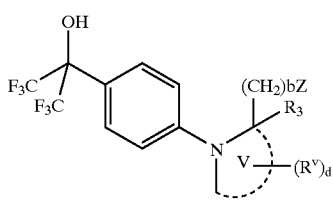

(Formula III)

wherein:
the ring denoted as V is a heterocyclic ring;
each $R^V$ is independently hydrogen, hydroxy, halo, alkyl, alkoxy, cyano, nitro or alkylthio;
d is 0–3; and
b, $R_3$ and Z are as defined in connection with Formula I.

In one such embodiment in which the LXR modulators correspond to Formula III, the V ring may define a heterocyclic ring, more typically a 5–6 member heterocyclic ring. For example, the V ring may be pyrrolidine or piperidine. In each of these embodiments, the V ring may optionally be substituted by one or more substituents (i.e., when d>0 and $R^V$ is other than hydrogen) selected, for example, from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In addition, when d is at least two and $R^V$ is other than hydrogen, two of the $R^V$ substituents may combine to form a fused ring (e.g., wherein the two $R^V$ substituents define a fused ring comprising a methylene dioxy or ethylene dioxy linkage).

In one such embodiment in which the LXR modulators correspond to Formula III, Z is —$CO_2Z_1$, —$CH_2NZ_1Z_2$, —$C(O)Z_1$, —$CH(OH)Z_1$, —$CH_2OZ_1$, —$CH_2OC(O)Z_1$, or —$C(O)NZ_1Z_2$, and $Z_1$ and $Z_2$ are independently hydrogen, or optionally substituted alkyl, heterocyclo, or aralkyl. In one embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In another embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, amino, aryl and heteroaryl. For example, in one embodiment, Z is —$CO_2Z_1$ and $Z_1$ is methyl, ethyl or other lower alkyl; in each of these embodiments the alkyl group may optionally be substituted with one or more of the aforementioned substituents. Alternatively, Z may be —$CH_2NZ_1Z_2$ wherein $Z_1$ and $Z_1$ are independently hydrogen, methyl, ethyl or other lower alkyl, methoxy or other lower alkoxy, benzyl, substituted benzyl and the like. Alternatively, Z may be —$C(O)Z_1$ wherein $Z_1$ is methyl, ethyl, propyl or other lower alkyl; in each of these embodiments the alkyl group may optionally be substituted with one or more of the aforementioned substituents. Alternatively, Z is —$CH(OH)Z_1$ wherein $Z_1$ is hydrogen, methyl, ethyl, propyl or other lower alkyl; in each of these embodiments the alkyl group may optionally be substituted with one or more of the aforementioned substituents. Alternatively, Z is —$CH_2OZ_1$ wherein $Z_1$ is methyl, ethyl, propyl or other lower alkyl; in each of these embodiments the alkyl group may optionally be substituted with one or more of the aforementioned substituents. Alternatively, Z is —$CH_2OC(O)Z_1$ wherein $Z_1$ is methyl, ethyl, propyl or other lower alkyl; in each of these embodiments the alkyl group may optionally be substituted with one or more of the aforementioned substituents. Alternatively, Z is —$C(O)NZ_1Z_2$ wherein $Z_1$ and $Z_1$ are independently hydrogen, methyl, ethyl or other lower alkyl, methoxy or other lower alkoxy, benzyl, substituted benzyl and the like. In addition, in each of these alternative embodiments, the V ring may define a heterocyclic ring, more typically a 5–6 member heterocyclic ring as previously described.

In a further embodiment, the LXR modulators correspond to Formula I wherein $R_4$ and $R_1$ together with the atoms to which they are attached form a fused heterocyclic ring. In this embodiment for example, the compounds correspond to Formula IV;

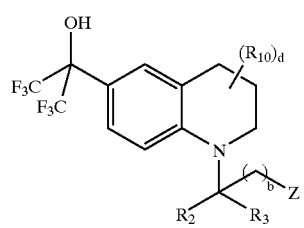

(Formula IV)

wherein:
each $R_{10}$ is independently hydrogen, hydroxy, halo, alkyl, alkoxy, cyano, nitro or alkylthio; and $R_3$ are independently hydrogen, alkyl, cycloalkyl, aryl, heteroaryl, aminoalkyl, hydroxyalkyl, or thioalkyl;
d is 0–3, and
b, $R_2$, $R_3$ and Z are as defined in connection with Formula I.

In one such embodiment in which the LXR modulators correspond to Formula IV, d is zero (or stated another way, d is greater than zero, but each $R^{10}$ is hydrogen). In another such embodiment, d is 1 and $R_{10}$ is hydroxy, chloro, fluoro, methyl, trihalomethyl, ethyl, methoxy, ethoxy, cyano or the like. In addition, when d is at least two and $R^{10}$ is other than hydrogen, two of the $R^{10}$ substituents may combine to form a fused ring (e.g., wherein the two $R^{10}$ substituents define a fused ring comprising a methylene dioxy or ethylene dioxy linkage).

In one such embodiment in which the LXR modulators correspond to Formula IV, Z is —$CO_2Z_1$, —$CH_2NZ_1Z_2$, —$C(O)Z_1$, —$CH(OH)Z_1$, —$CH_2OZ_1$, —$CH_2OC(O)Z_1$, or —$C(O)NZ_1Z_2$, and $Z_1$ and $Z_2$ are independently hydrogen, or optionally substituted alkyl, heterocyclo, or aralkyl. In one embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In another embodiment, the substituent(s) of the optionally substituted alkyl, heterocyclo or aralkyl are selected from halogen, haloalkyl, hydroxy, hydroxyalkyl, lower alkyl, alkoxy, cyano, nitro, alkylthio, amino, aryl and heteroaryl. For example, in one embodiment, Z is —$CO_2Z_1$ and $Z_1$ is methyl, ethyl or other lower alkyl; in each of these embodiments the alkyl group may optionally be substituted with one or more of the aforementioned substituents. Alternatively, Z may be —$CH_2NZ_1Z_2$ wherein $Z_1$ and $Z_1$ are independently hydrogen, methyl, ethyl or other lower alkyl, methoxy or other lower alkoxy, benzyl, substituted benzyl and the like. Alternatively, Z may be —$C(O)Z_1$ wherein $Z_1$ is methyl, ethyl, propyl or other lower alkyl; in each of these embodiments the alkyl group may optionally be substituted with one or more of the aforementioned substituents. Alternatively, Z is —$CH(OH)Z_1$ wherein $Z_1$ is hydrogen, methyl, ethyl, propyl or other lower alkyl; in each of these embodiments the alkyl group may optionally be substituted with one or more of the aforementioned substituents. Alternatively, Z is —$CH_2OZ_1$ wherein $Z_1$ is methyl, ethyl, propyl or other lower alkyl; in each of these embodiments the alkyl group may optionally be substituted with one or more of the aforementioned substituents. Alternatively, Z is —$CH_2OC(O)Z_1$ wherein $Z_1$ is methyl, ethyl, propyl or other lower alkyl; in each of these embodiments the alkyl group may optionally be substituted with one or more of the aforementioned substituents. Alternatively, Z is —$C(O)NZ_1Z_2$ wherein $Z_1$ and $Z_1$ are independently hydrogen, methyl, ethyl or other lower alkyl, methoxy or other lower alkoxy, benzyl, substituted benzyl and the like.

Another aspect of the present invention are the prodrugs of the compounds corresponding to the formulae disclosed herein, which are converted under physiological conditions to the biologically active drug by any of a number of chemical and biological mechanisms. In general terms, these prodrug conversion mechanisms are hydrolysis, reduction, oxidation, and elimination.

A further aspect of the invention encompasses conversion of the prodrug to the biologically active drug by elimination of the prodrug moiety. Generally speaking, in this embodiment the prodrug moiety is removed under physiological conditions with a chemical or biological reaction. The elimination results in removal of the prodrug moiety and liberation of the biologically active drug. Any compound of the present invention corresponding to any of the formulas disclosed herein may undergo any combination of the above detailed mechanisms to convert the prodrug to the biologically active compound. For example, a particular compound may undergo hydrolysis, oxidation, elimination, and reduction to convert the prodrug to the biologically active compound. Equally, a particular compound may undergo only one of these mechanisms to convert the prodrug to the biologically active compound.

The compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of any of the formulae disclosed herein. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures or R and S forms for each stereocenter present.

Formulation

Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric, and galacturonic acids.

Suitable pharmaceutically-acceptable base addition salts of compounds used in connection with the present invention include metallic ion salts and organic ion salts. More preferred metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention. Pharmaceutically acceptable esters include, but are not limited to, the alkyl esters of the LXR modulators.

The Liver X-Receptor (LXR) modulators described in the present invention may be used to treat, prevent or reduce atherosclerosis. Without being bound by any particular theory, it is presently believed that activation of LXR by a small molecule ligand will lead to an up-regulation of ABCA1 and induction of the reverse cholesterol transport pathway thereby increasing cholesterol efflux to HDL-C and reducing the cholesterol content of atherosclerotic plaques.

Administration

For methods of prevention, the subject is any human or animal subject, and preferably is a subject that is in need of prevention and/or treatment of atherosclerosis. The subject may be a human subject who is at risk for atherosclerosis. The subject may be at risk for atherosclerosis due to genetic predisposition, lifestyle, diet, exposure to disorder-causing agents, exposure to pathogenic agents and the like.

In general, therefore, one aspect of the present invention is the administration of a composition comprising an Liver X-Receptor modulator or a pharmaceutically acceptable salt for the treatment, prevention or removal of cholesterol deposition in vessel walls. The amount of LXR modulator that is used will generally be in the range of about 0.001 to about 100 milligrams per day per kilogram of body weight of the subject (mg/day·kg), more preferably from about 0.05 to about 50 mg/day-kg, even more preferably from about 0.1 to about 10 mg/day·kg. Those skilled in the art, however, will appreciate that dosages may also be determined with guidance from Goodman & Goldman's *The Pharmacological Basis of Therapeutics*, Ninth Edition (1996), Appendix II, pp. 1707–1711 and from Goodman & Goldman's *The Pharmacological Basis of Therapeutics*, Tenth Edition (2001), Appendix II, pp. 475–493. In addition, the LXR modulators of the present invention may be provided in a therapeutic composition so that the preferred amount is supplied by a single dosage, a single capsule for example, or, by up to four, or more, single dosage forms.

The LXR pharmaceutical composition(s), analog, hydrolysis product, metabolite or precursor may be administered enterally and parenterally. Parenteral administration includes subcutaneous, intramuscular, intradermal, intramammary, intravenous, and other administrative methods known in the art. Enteral administration includes solution, tablets, sustained release capsules, enteric coated capsules, and syrups. When administered, the pharmaceutical composition may be at or near body temperature.

The phrases "therapeutically-effective" and "effective for the treatment, prevention, or reduction", are intended to qualify the amount of each LXR agent and for use in the LXR therapy which will achieve the goal of reduction of the severity and/or frequency of incidence of atherosclerosis associated symptoms, while avoiding adverse side effects typically associated with alternative therapies.

In particular, the pharmaceutical composition of an LXR modulator and in connection with the method(s) of the present invention can be administered orally, for example, as tablets, coated tablets, dragees, troches, lozenges, gums, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin, or olive oil.

Aqueous suspensions can be produced that contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate.

The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the active ingredients in an omega-3 fatty acid, a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present. Syrups and elixirs containing the novel combination may be formulated with sweetening agents, for example glycerol, sorbitol or sucrose. Such formulations may also contain a demulcent, a preservative and flavoring and coloring agents.

The subject pharmaceutical composition of LXR modulators in connection with the present inventive method can also be administered parenterally, either subcutaneously, or intravenously, or intramuscularly, or intrasternally, or by infusion techniques, in the form of sterile injectable aqueous or olagenous suspensions. Such suspensions may be formulated according to the known art using those suitable dispersing of wetting agents and suspending agents which have been mentioned above, or other acceptable agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, n-3 polyunsaturated fatty acids may find use in the preparation of injectables.

The subject pharmaceutical composition of LXR modulators and in connection with the present inventive method can also be administered by inhalation, in the form of aerosols or solutions for nebulizers, or rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

The pharmaceutical compositions of LXR modulators and in connection with the present inventive method can also be administered topically, in the form of patches, creams, ointments, jellies, collyriums, solutions or suspensions. Of course, the compositions of the present invention can be administered by routes of administration other than topical administration. Also, as mentioned above, the LXR modulators and may be administered separately, with each agent administered by any of the above mentioned administration routes. For example, the LXR modulators may be administered orally in any or the above mentioned forms (e.g. in capsule form) while the is administered topically (e.g. as a cream).

Daily dosages can vary within wide limits and will be adjusted to the individual requirements in each particular case. In general, for administration to adults, an appropriate daily dosage has been described above, although the limits that were identified as being preferred may be exceeded if expedient. The daily dosage can be administered as a single dosage or in divided dosages.

The pharmaceutical composition may optionally contain, in addition to the LXR modulator, another lipid modulating agent such as a statin, resin, niacin or other cholesterol absorption inhibitor. Alternatively, these other lipid modulating agents may be administered separately but in conjunction with the LXR modulator as part of a co-therapy.

Synthesis

Compounds of the present invention can be prepared by a variety of methods. Aniline (i) can be functionalized with hexafluoroacetone to give aniline (ii) followed by reductive alkylation to form (iii) (Scheme 1, Method A). Other compounds of the present invention can be prepared by reductive alkylation of (i) to form (iv), alkylation to give (v) followed by treatment with hexafluoroacetone to afford (vi) (Scheme 1, Method B).

Other compounds of the present invention can be prepared by alkylation of (vii) to give (viii) followed by treatment with hexafluoroacetone to form (ix) (Scheme 2, Method C). Alternatively, (ix) can be formed by reaction with hexafluoroacetone to give (x) which is then alkylated to give (ix) (Scheme 2, Method D).

Other compounds of the present invention can be prepared from aniline (xi) or (ii) (Scheme 3). Aniline (xii) can be reacted with dimethyl diazomalonate to form (xiii). Ester hydrolysis, decarboxylation and esterification can then be completed to give (xiv).

Other compounds of the present invention can be prepared through the addition of an aldehyde or ketone and trimethylsilyl cyanide to aniline (ii) to give (xv) which is then esterified to give (xvi) (Scheme 4).

Other compounds of the present invention can be prepared by reaction of aniline (ii) with acetone cyanohydrin to give (xvii) which is then esterified to give (xviii) (Scheme 5).

Other compounds of the present invention can be prepared by addition of aniline (xii) to ethyl acrylate to give (xix) (Scheme 6).

Other compounds of the present invention can be prepared by reaction of substituted amine (xx) with triphenylbismuth diacetate and copper(II) acetate to form (xxi) followed by treatment with hexafluoroacetone to give (xxii) (Scheme 7).

Other compounds of the present invention can be prepared by hydrolysis of ester (xxiii) to form acid (xxiv) which can then be converted to amides in the usual manner to give (xxv) or differentially esterified to (xxiii). Alternatively ester (xxiii) can be reduced to give (xxvi) (Scheme 8).

Other compounds of the present invention can be prepared by alkylation of the alcohol (xxvii) followed by treatment with hexafluoroacetone to give ether (xxviii). Alternatively alcohol (xxvii) can be O-acylated and treated with hexafluoroacetone to give ester (xxix) (Scheme 9).

Other compounds of the present invention can be prepared by addition of a Grignard reagent to the Weinreb amide (xxx) to afford the ketone (xxxi). Ketone (xxxi) can be reduced in the usual manner to afford the alcohol (xxxii) (Scheme 10).

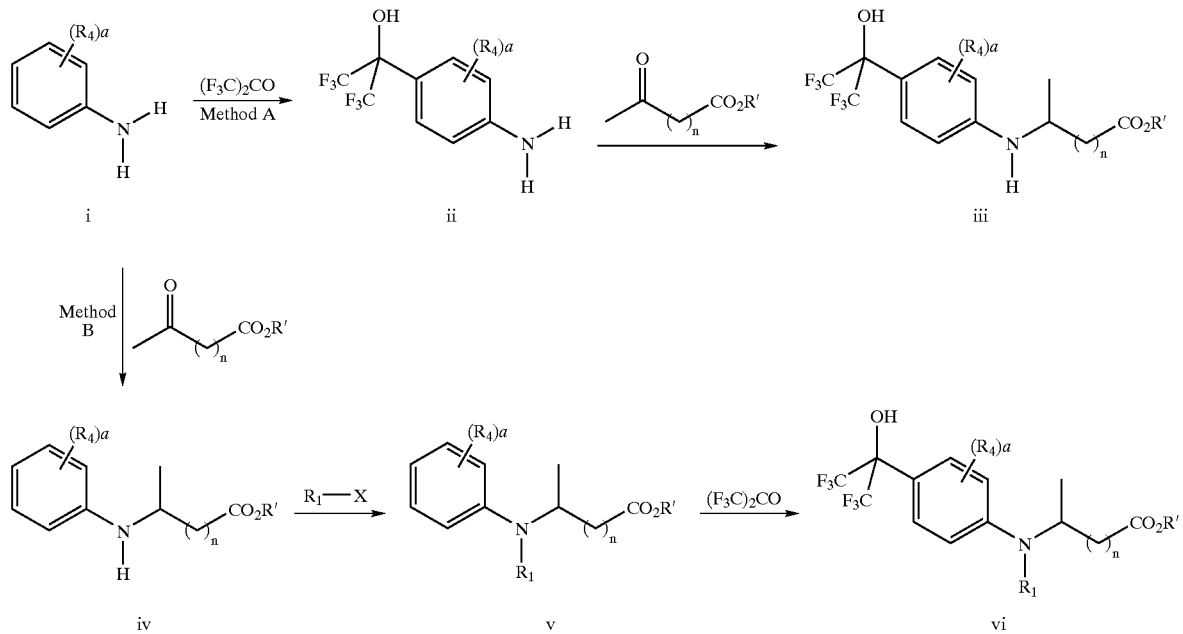

Scheme 2
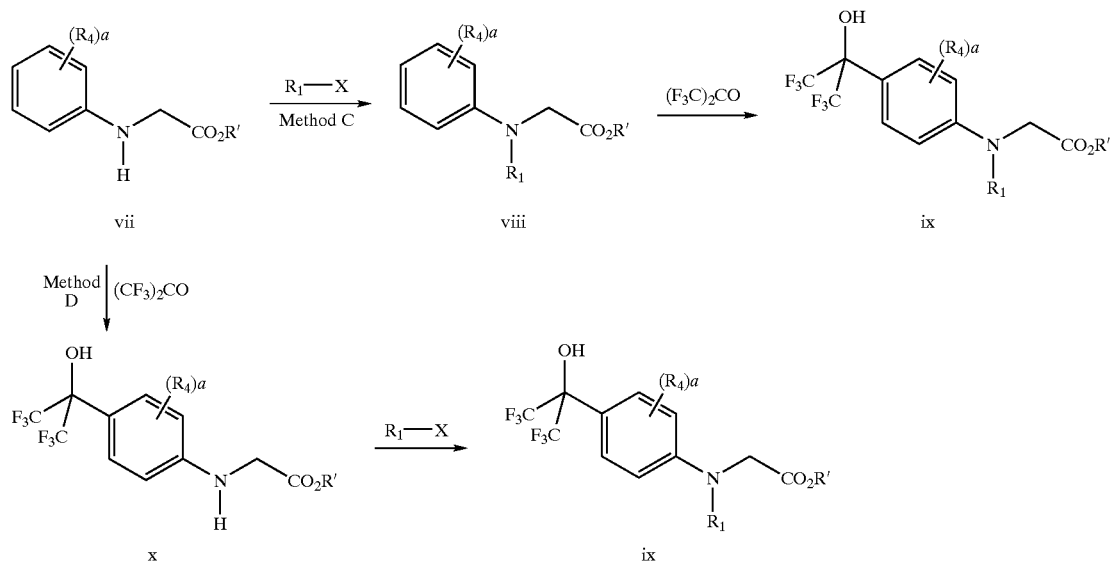
Scheme 3
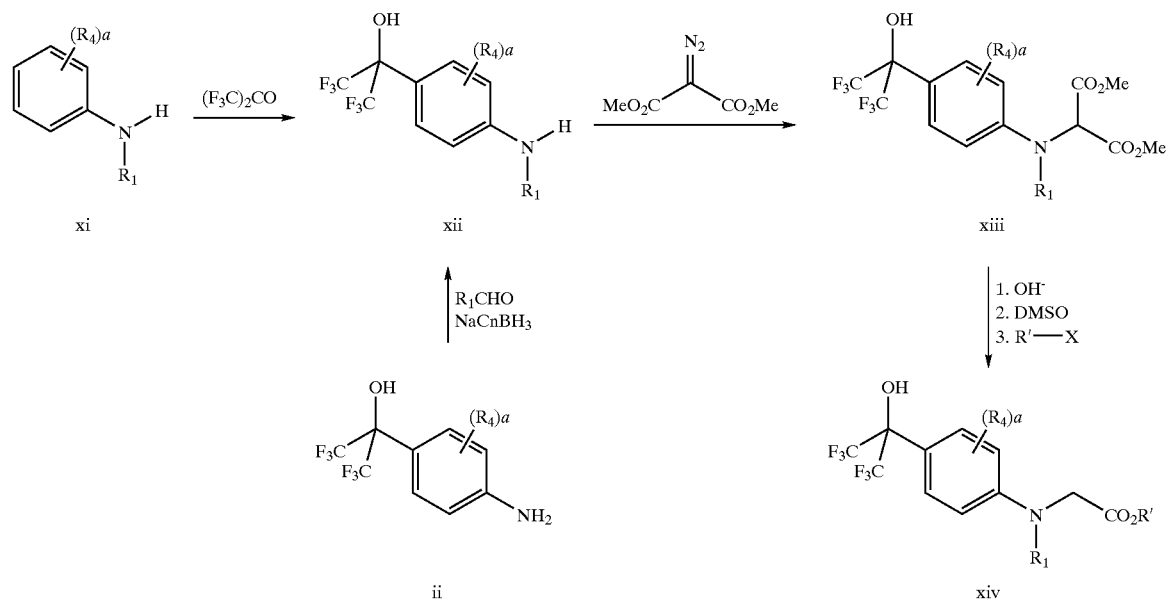
Scheme 4
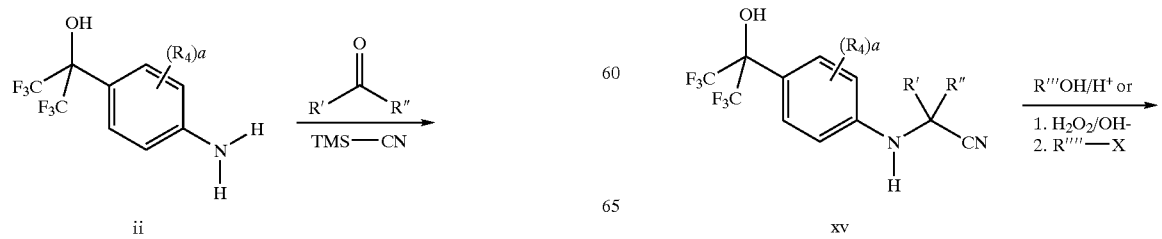

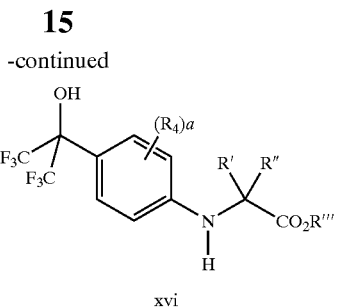
xvi
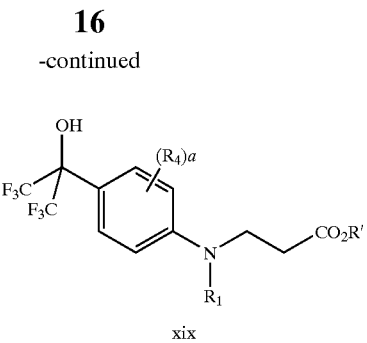
xix
Scheme 5
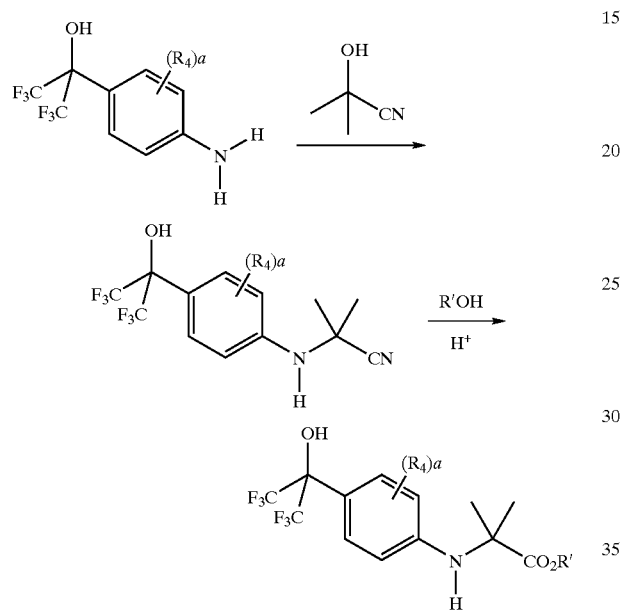
Scheme 6
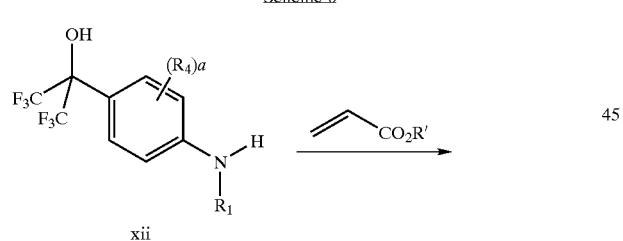
xii
Scheme 7
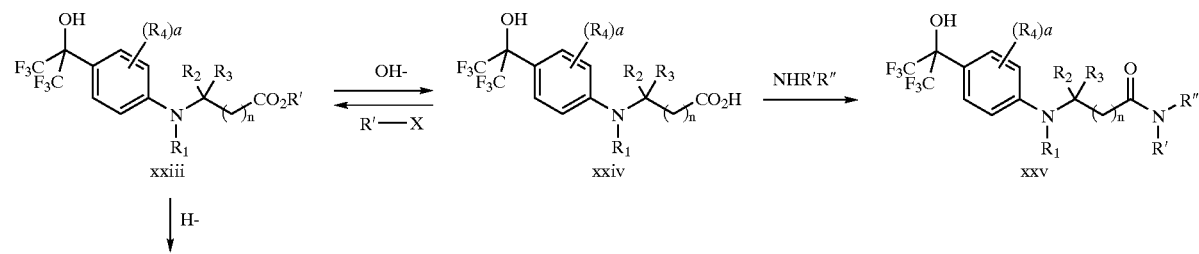
Scheme 8

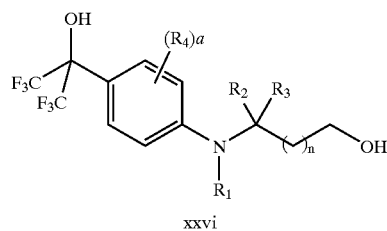

xxvi

Scheme 9

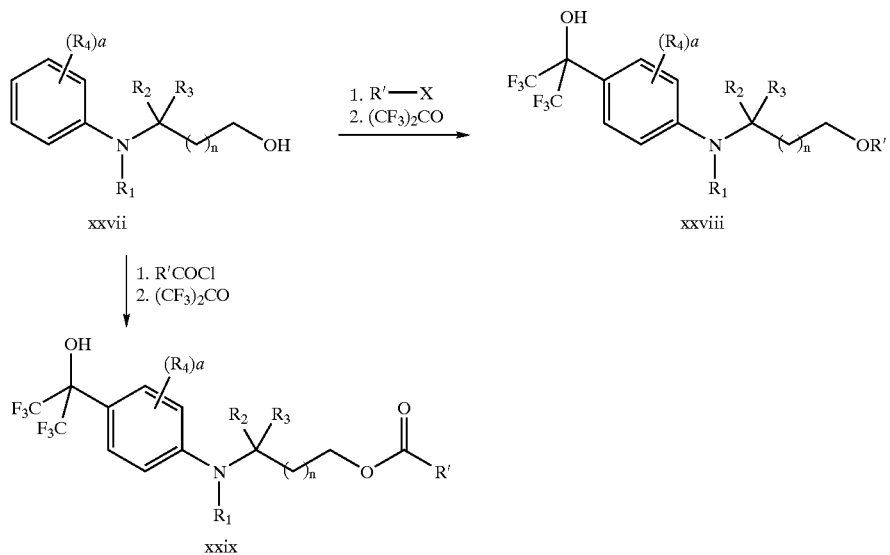

Scheme 10

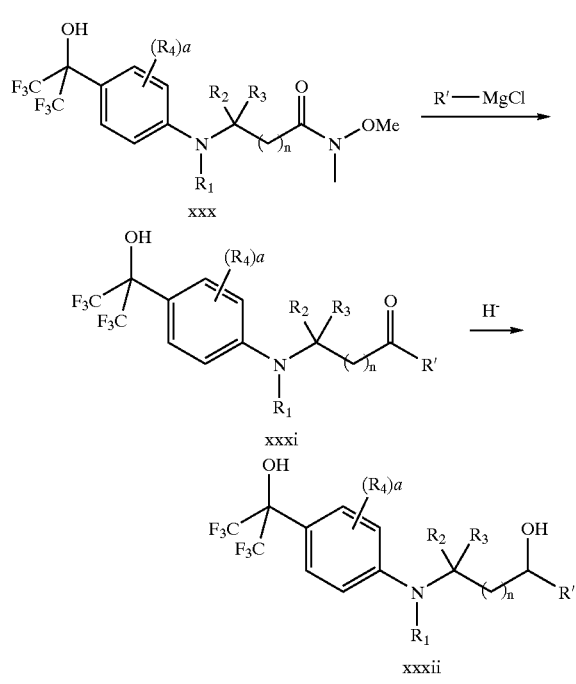

Definitions

The term "acyl," as used herein alone or as part of another group, denotes the moiety formed by removal of the hydroxyl group from the —COOH group of an organic carboxylic acid, e.g., RC(O)— wherein R is $R_a$, $R_aO$—, $R_aS$—, or $R_aR_bN$—, $R_a$ and $R_b$ are independently hydrogen, hydrocarbyl, substituted hydrocarbyl, or heterocyclo and "—" denotes the point of attachment.

The term "acylamino," as used herein alone or as part of another group, denotes an acyl group as defined above, bonded through a nitrogen atom, e.g., $RC(O)N(R_c)$— wherein R is as defined in connection with the term "acyl", $R_c$ is hydrogen, hyrocarbyl, or substituted hydrocarbyl, and "—" denotes the point of attachment.

The term "acyloxy" as used herein alone or as part of another group, denotes an acyl group as defined above, bonded through an oxygen atom (—O—), e.g., RC(O)O— wherein R is as defined in connection with the term "acyl" and "—" denotes the point of attachment.

The term "acylthio" as used herein alone or as part of another group, denotes an acyl group as defined above, bonded through a sulfur atom (—S—), e.g., RC(O)S— wherein R is as defined in connection with the term "acyl" and "—" denotes the point of attachment.

The term "alkaryl" as used herein alone or as part of another group denotes a mixed alkyl/aryl moieity with the point of attachment being to the alkyl portion, e.g., benzyl (—$CH_2C_6H_5$ wherein "—" denotes the point of attachment)

The term "amino" as used herein alone or as part of another group shall denote a primary, secondary or tertiary amine which may optionally be hydrocarbyl, substituted hydrocarbyl or heteroatom substituted. Specifically included are secondary or tertiary amine nitrogens which are members of a heterocyclic ring. Also specifically included, for example, are secondary or tertiary amino groups substituted by an acyl moiety.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" shall mean aryl or heteroaromatic.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

As used herein, an "effective amount" or "therapeutically effective amount" means the dose or effective amount to be administered to a patient and the frequency of administration to the subject which is sufficient to obtain a therapeutic effect as readily determined by one of ordinary skill in the art, by the use of known techniques and by observing results obtained under analogous circumstances. The dose or effective amount to be administered to a patient and the frequency of administration to the subject can be readily determined by one of ordinary skill in the art by the use of known techniques and by observing results obtained under analogous circumstances. In determining the effective amount or dose, a number of factors are considered by the attending diagnostician, including but not limited to, the potency and duration of action of the compounds used; the nature and severity of the illness to be treated as well as on the sex, age, weight, general health and individual responsiveness of the patient to be treated, and other relevant circumstances.

The phrase "therapeutically effective" indicates the capability of an agent to prevent, or reduce the severity of, the disorder or its undesirable symptoms, while avoiding adverse side effects typically associated with alternative therapies.

The term "pharmacologically effective amount" shall mean that amount of a drug or pharmaceutical agent that will elicit the biological or medical response of a tissue, system, animal or human that is being sought. This amount can be a therapeutically effective amount.

The term "pharmaceutically acceptable" is used herein to mean that the agent or adjuvant is appropriate for use in a pharmaceutical product. Pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

The term "subject" for purposes of treatment includes any human or animal subject who is in need of the treatment, prevention or inhibition of an LXR-mediated disorder. The subject is typically a human subject.

Unless otherwise indicated herein, the term "substituted" as used, for example, in connection with any of the moieties described herein shall mean moieties which are substituted with a hydrocarbyl moiety, a substituted hydrocarbyl moiety, a heteroatom, or a heterocyclo. For example, substituents include moieties in which a carbon atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

Other embodiments within the scope of the embodiments herein will be apparent to one skilled in the art from consideration of the specification or practice of the invention as disclosed herein. It is intended that the specification be considered to be exemplary only, with the scope and spirit of the invention being indicated by the embodiments.

As various changes could be made in the above methods and compositions without departing from the scope of the invention, it is intended that all matter contained in this application shall be interpreted as illustrative and not in a limiting sense.

The following examples illustrate the invention.

EXAMPLE 1

Ethyl 3-({4-[2,2,2-trifluoro-1-hydroxy-1-(trifluoromethyl)ethyl]phenyl}amino)-butanoate

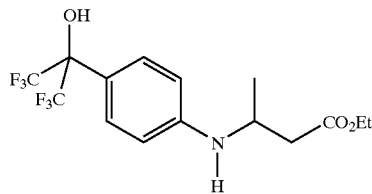

Step 1
2-(4-Aminophenyl)-1,1,1,3,3,3-hexafluoropropan-2-ol

A neat solution of aniline (4.3 mL, 47 mmol) and p-toluenesulfonic acid monohydrate (85 mg, 0.45 mmol) in a round bottom flask equipped with a reflux condenser was heated to 90° C. and hexafluoroacetone trihydrate (7 mL, 50 mmol) added over 15 minutes via syringe. Following addition, the temperature was increased to 130° C. and the resulting solution stirred over 18 h. The reaction mixture was cooled to room temperature and diluted with ethyl acetate. The organics were washed with saturated $NaHCO_3$ solution then brine. The solution was dried over $MgSO_4$ and the solvent removed in vacuo. The residue was purified by flash chromatography (4:1 hexanes/EtOAc) to give the title product as a white crystalline solid (5.5 g, 45%). MS (ES+) m/z 260 (MH+).

Step 2
Ethyl 3-({4-[2,2,2-trifluoro-1-hydroxy-1-(trifluoromethyl)ethyl]phenyl}amino)-butanoate The product from step 1 (500 mg, 1.9 mmol) and ethyl acetoacetate (0.27 mL, 2.1 mmol) were combined and dissolved in methanol (10 mL) at ambient temperature. To this solution was added glacial acetic acid (0.13 mL, 2.1 mmol) followed by sodium cyanoborohydride (194 mg, 3.1 mmol). After stirring 18 h, the solution was concentrated in vacuo and the resultant oil dissolved in ethyl acetate. The organics were washed with brine, dried over $MgSO_4$, and concentrated. Purification by reverse phase HPLC using a gradient elution of 60:40 $H_2O$/TFA:$CH_3CN$ to 0:100 $H_2O$/TFA:$CH_3CN$ at 254 nm afforded the title compound as a white solid (440 mg, 61%): mp=103° C.

$^1$H NMR ($CDCl_3$) δ 7.43 (d, 2H), 6.64 (d, 2H), 4.07 (q, 2H), 3.90 (m, 1H), 3.43 (br s, 1H), 2.58 (dd, 1H), 2.41 (dd, 1H), 1.23 (d, 3H), 1.17 (t, 3H). MS (ES+) m/z 374 (MH+). Anal. Calc. for $C_{15}H_{17}NO_3F_6$: C, 48.26; H, 4.59; N, 3.75. Found: C, 47.95; H, 4.45; N, 3.58.

EXAMPLE 2

Ethyl N-methyl-N-{4-[2,2,2-trifluoro-1-hydroxy-1-(trifluoromethyl)ethyl]phenyl}-alaninate

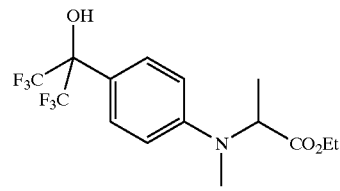

Step 1
Ethyl N-phenylalaninate

Prepared as a light yellow oil in the manner of Example 1 step 2 (41%) except aniline was substituted for 2-(4-aminophenyl)-1,1,1,3,3,3-hexafluoropropan-2-ol. MS (ES+) m/z 194 (MH+).

Step 2
Ethyl N-methyl-N-phenylalaninate

To a solution of ethyl N-phenylalaninate (2 g, 10.3 mmol) in DMF (103 mL) was added powdered potassium carbonate (2.6 g, 18.5 mmol) followed by iodomethane (1.03 mL, 16.6 mmol) and the resulting mixture was heated at 70° C. over 3 days. The reaction mixture was cooled to room temperature and diluted with 1 M HCl and ethyl acetate. The product was extracted 3 times with ethyl acetate and the combined organics washed with brine, dried ($MgSO_4$), and concentrated in vacuo. Purification by flash chromatography (8:1 hexanes/EtOAc) yielded the title compound as a colorless oil (725 mg, 34%). MS (ES+) m/z 208 (MH+).

Step 3
Ethyl N-methyl-N-{4-[2,2,2-trifluoro-1-hydroxy-1-(trifluoromethyl)ethyl]phenyl}-alaninate Prepared in the manner of Example 1 step 1 except ethyl N-methyl-N-phenylalaninate was substituted for aniline. Purification by reverse phase HPLC using a gradient elution of 60:40 $H_2O$/TFA:$CH_3CN$ to 0:100 $H_2O$/TFA:$CH_3CN$ at 254 nm afforded the title compound as a colorless oil (85%).

$^1$H NMR ($CDCl_3$) δ 7.56 (d, 2H), 6.84 (s, 2H), 4.56 (m, 1H), 4.19 (m, 2H), 3.44 (br s, 1H), 2.96 (s, 3H), 1.53 (d, 3H), 1.24 (t, 3H). MS (ES+) m/z 374 (MH+). Anal. Calc. for $C_{15}H_{17}NO_3F_6$: C, 48.26; H, 4.59; N, 3.75. Found: C, 47.98; H, 4.38; N, 3.63.

EXAMPLE 3

Ethyl 2-methyl-N-{4-[2,2,2-trifluoro-1-hydroxy-1-(trifluoromethyl)ethyl]phenyl}-alaninate

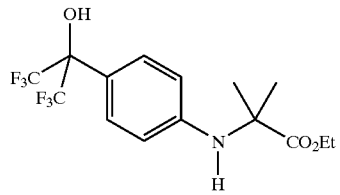

Step 1
2-Methyl-2-({4-[2,2,2-trifluoro-1-hydroxy-1-(trifluoromethyl)ethyl]phenyl}-amino)propanenitrile A solution of 2-(4-aminophenyl)-1,1,1,3,3,3-hexafluoropropan-2-ol (Oakwood, 5.0 g, 19.3 mmol) and acetone cyanohydrin (3.6 mL, 39.8 mmol) in THF (19 mL) was heated at reflux over 24 h. After cooling, the reaction mixture was diluted with EtOAc and washed several times with brine. Purification by reverse phase HPLC using a gradient elution of 60:40 $H_2O$/TFA:$CH_3CN$ to 0:100 $H_2O$/TFA:$CH_3CN$ at 254 nm afforded the title compound as a white powder (2.76 g, 44%). MS (ES+) m/z 327 (MH+).

Step 2
Ethyl 2-methyl-N-{4-[2,2,2-trifluoro-1-hydroxy-1-(trifluoromethyl)ethyl]phenyl}-alaninate The product from step 1 (1 g, 3.07 mmol) was added to sulfuric acid (0.8 mL) at ambient temperature and stirred 2.5 h. Absolute ethanol (1.8 mL) was added and the resulting solution heated at reflux over 3 h. The solution was cooled to room temperature and treated with 1 M NaOH until a pH=8 was reached. The product was extracted with ethyl acetate and the combined organics washed with brine, dried ($MgSO_4$), and concentrated in vacuo. Purification by reverse phase HPLC using a gradient elution of 60:40 $H_2O$/TFA:$CH_3CN$ to 0:100 $H_2O$/TFA:$CH_3CN$ at 254 nm afforded the title compound as a light pink solid (45%): mp=93° C. $^1$H NMR (CDCl$_3$) δ 7.58 (d, 2H), 6.77 (s, 2H), 4.29 (q, 2H), 3.50 (br s, 1H), 1.71 (s, 6H), 1.29 (t, 3H). MS (ES+) m/z 374 (MH+). Anal. Calc. for $C_{15}H_{17}NO_3F_6$: C, 48.26; H, 4.59; N, 3.75. Found: C, 48.00; H, 4.51; N, 3.59.

EXAMPLE 4

Ethyl 1-{4-[2,2,2-trifluoro-1-hydroxy-1-(trifluoromethyl)ethyl]phenyl}piperidine-2-carboxylate

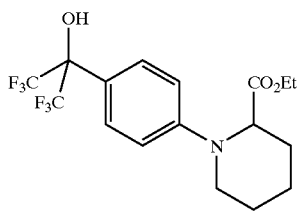

Step 1
Ethyl 1-phenylpiperidine-2-carboxylate

Triphenylbismuth diacetate (2 g, 3.5 mmol) and copper (II) acetate (58 mg, 0.3 mmol) were added to a solution of ethyl pipecolinate in $CH_2Cl_2$ (16 mL). After stirring 18 h at ambient temperature, the mixture was diluted with water and extracted with several portions of $CH_2Cl_2$. The combined organics were washed with water and dried ($MgSO_4$). Concentration in vacuo afforded a colorless oil (850 mg, crude). MS (ES+) m/z 234 (MH+).

Step 2
Ethyl 1-{4-[2,2,2-trifluoro-1-hydroxy-1-(trifluoromethyl)ethyl]phenyl}piperidine-2-carboxylate Prepared in the manner of Example 1 step 1 except ethyl 1-phenylpiperidine-2-carboxylate was substituted for aniline. Purification by reverse phase HPLC using a gradient elution of 60:40 $H_2O$/TFA:$CH_3CN$ to 0:100 $H_2O$/TFA:$CH_3CN$ at 254 nm afforded the title compound as a colorless oil (21%). $^1$H NMR (CDCl$_3$) δ 7.51 (d, 2H), 7.21 (d, 2H), 4.38 (m, 1H), 4.05 (m, 2H), 3.65–3.52 (m, 2H), 2.38–2.20 (m, 2H), 1.64–1.49 (m, 4H), 1.04 (t, 3H), MS (ES+) m/z 400 (MH+). Anal. Calc. for $C_{17}H_{19}NO_3F_6$: C, 51.13; H, 4.80; N, 3.51. Found: C, 50.85; H, 4.75; N, 3.40.

EXAMPLE 5

Ethyl N-(2,2,2-trifluoroethyl)-N-{4-[2,2,2-trifluoro-1-hydroxy-1-(trifluoromethyl)-ethyl]phenyl}glycinate

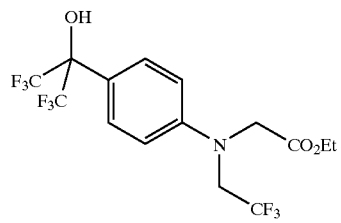

Step 1
1,1,1,3,3,3-Hexafluoro-2-{4-[(2,2,2-trifluoroethyl)amino]phenyl}propan-2-ol To a suspension of 2-(4-aminophenyl)-1,1,1,3,3,3-hexafluoropropan-2-ol (Oakwood, 8.4 g, 28.4 mmol) in $CH_2Cl_2$ (75 mL) was added trifluoroacetic anhydride (4.4 mL, 31.2 mmol) via addition funnel over 30 min. After stirring at ambient temperature overnight, the reaction mixture was diluted with ethyl acetate and washed with water, saturated $NaHCO_3$, and brine. The organics were dried ($MgSO_4$), filtered and concentrated to afford the intermediate amide as a white solid. The amide was dissolved in anhydrous THF (75 mL) and lithium aluminum hydride (1M solution in THF, 75 mL) added over 30 min. After stirring at ambient temperature for 30 min, the solution was heated at reflux over 18 h. The reaction mixture was cooled to room temperature and quenched under argon with ethyl acetate. Water was carefully added and the resulting mixture stirred 30 min. The mixture was filtered through a pad of celite and the filtrate concentrated in vacuo. The resulting oil was dissolved in ethyl acetate and washed several times with brine. The organics were dried ($MgSO_4$) and concentrated to afford the title compound as a yellow oil (5.6 g, 58%). MS (ES+) m/z 342 (MH+).

Step 2

Dimethyl 2-((2,2,2-trifluoroethyl){4-[2,2,2-trifluoro-1-hydroxy-1-(trifluoromethyl)-ethyl]phenyl}amino)malonate The product from step 1 (500 mg, 1.47 mmol), dimethyl diazomalonate (220 mg, 1.4 mmol, prepared via Synthetic Comm., 17 (14), 1709–16 (1987)), and rhodium acetate (65 mg, 0.015 mmol) were combined and dissolved in $CH_2Cl_2$ (12 mL). The resulting mixture was heated at reflux over 1.5 h, cooled to room temperature, and concentrated in vacuo.

Purification by flash chromatography (4:1 hexanes/EtOAc) afforded the title compound as a colorless oil (626 mg, 95%). MS (ES+) m/z 472 (MH+).

Step 3

N-(2,2,2-Trifluoroethyl)-N-{4-[2,2,2-trifluoro-1-hydroxy-1-(trifluoromethyl)-ethyl]phenyl}glycine The product from step 2 (660 mg, 1.4 mmol) was dissolved in methanol (14 mL) and 1M NaOH (7 mL) added. After warming the reaction mixture at 60° C. for 18 h, it was cooled and 1M HCl added until a pH=3 was reached. The di-acid was extracted into ethyl acetate, dried (MgSO$_4$), and concentrated. The resulting oil was dissolved in DMSO (3 mL) and heated at 100° C. for 2 h. After cooling to ambient temperature, ethyl acetate was added followed by 1M HCl. The organics were washed with brine, dried (MgSO$_4$), and concentrated in vacuo. The title acid was isolated as a white solid (431 mg, 77%). MS (ES+) m/z 400 (MH+).

Step 4

Ethyl N-(2,2,2-trifluoroethyl)-N-{4-[2,2,2-trifluoro-1-hydroxy-1-(trifluoromethyl)-ethyl]phenyl}glycinate The product from step 3 (300 mg, 0.75 mmol) was dissolved in DMF (4 mL) and powdered potassium carbonate (207 mg, 1.5 mmol) added. Ethyl triflate (0.1 mL, 0.75 mmol) was slowly added via syringe and the resulting solution stirred over 2 h. The solution was diluted with ethyl acetate, washed with saturated NaHCO$_3$, dried (MgSO$_4$), and concentrated in vacuo. Purification by reverse phase HPLC using a gradient elution of 60:40 H$_2$O/TFA:CH$_3$CN to 0:100 H$_2$O/TFA:CH$_3$CN at 254 nm afforded the title compound as a white solid (311 mg, 97%): mp=67° C. $^1$H NMR (CDCl$_3$) δ 7.47 (d, 2H), 6.78 (d, 2H), 4.25 (q, 2H), 4.14 (s, 2H), 4.01 (q, 2H), 1.30 (t, 3H). MS (ES+) m/z 428 (MH+). Anal. Calc. for C$_{15}$H$_{14}$NO$_3$F$_9$: C, 42.17; H, 3.30; N, 3.28. Found: C, 42.30; H, 2.99; N, 3.16.

EXAMPLE 6

Ethyl N-ethyl-N-{4-[2,2,2-trifluoro-1-hydroxy-1-(trifluoromethyl)ethyl]-phenyl}glycinate

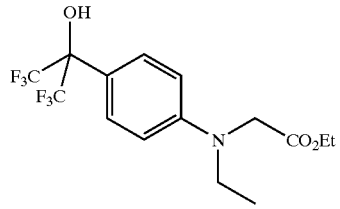

Step 1

Ethyl N-ethyl-N-phenylglycinate

NaH (224 mg, 5.6 mmol of 60% dispersion) was washed 3 times with hexanes and dried via vacuum aspiration. To the dry NaH was added a solution of N-phenylglycine ethyl ester (1 g, 5.6 mmol) in THF (28 mL) at 0° C. After stirring 1.5 h, ethyl triflate (0.7 mL, 5.6 mmol) was added via syringe. The resulting solution was stirred at ambient temperature over 18 h. The mixture was diluted with ethyl acetate and washed with 1M HCl and brine. The organics were dried (MgSO$_4$) and concentrated in vacuo. Purification by flash chromatography (4:1 hexanes/EtOAc) afforded the title compound as a light yellow oil (200 mg, 17%). MS (ES+) m/z 208 (MH+).

Step 2

Ethyl N-ethyl-N-{4-[2,2,2-trifluoro-1-hydroxy-1-(trifluoromethyl)ethyl]-phenyl}glycinate Prepared in the manner of Example 1 step 1 except ethyl N-ethyl-N-phenylglycinate was substituted for aniline. Purification by reverse phase HPLC using a gradient elution of 60:40 H$_2$O/TFA:CH$_3$CN to 0:100 H$_2$O/TFA:CH$_3$CN at 254 nm afforded the title compound as a colorless oil (87%). $^1$H NMR (CDCl$_3$) δ 7.51 (d, 2H), 6.69 (d, 2H), 4.23 (q, 2H), 4.04 (s, 2H), 3.51 (m, 3H), 1.26 (m, 6H). MS (ES+) m/z 374 (MH+). Anal. Calc. for C$_{15}$H$_{17}$NO$_3$F$_6$: C, 48.28; H, 4.59; N, 3.75. Found: C, 48.40; H, 4.96; N, 3.65.

EXAMPLE 7

Ethyl N-methyl-N-{4-[2,2,2-trifluoro-1-hydroxy-1-(trifluoromethyl)ethyl]-phenyl}glycinate

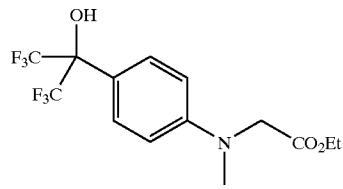

Prepared according to Example 2 steps 2 and 3 except with ethyl N-phenylglycinate instead of ethyl N-phenylalaninate. Title compound was obtained as a yellow solid (74%). $^1$H NMR (CDCl$_3$) δ 7.46 (d, 2H), 6.64 (d, 2H), 4.12 (q, 2H), 4.01 (s, 2H), 3.30 (s, 3H), 1.17 (t, 3H). Anal. Calc. for C$_{14}$H$_{15}$NO$_3$F$_6$: C, 46.80; H, 4.21; N, 3.90. Found: C, 47.78; H, 4.06; N, 3.86. HRMS (MH+) Calc.: 360.1047. Found: 360.1034.

EXAMPLE 8

Methyl phenyl({4-[2,2,2-trifluoro-1-hydroxy-1-(trifluoromethyl)ethyl]phenyl}amino)acetate hydrochloride

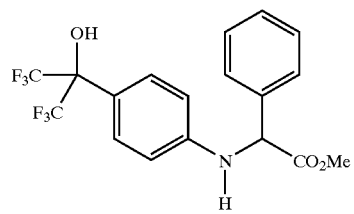

To a solution of 2-(4-aminophenyl)-1,1,1,3,3,3-hexafluoropropan-2-ol (Oakwood, 1.5 g, 5.8 mmol) in THF (25 mL) was added lithium bis(trimethyl)amide (11.6 mL of a 1.0 M solution in THF). After stirring for 10 minutes, methyl α-bromophenylacetate (1.3 g, 5.8 mmol) was added. The reaction mixture was stirred at room temperature for 18 h. The mixture was diluted with ethyl acetate and washed with water and brine. The organic solution was dried (MgSO$_4$) and concentrated in vacuo. Purification by flash chromatography (4:1 hexanes/EtOAc) gave the free base of the title compound. A solution of the free base in CH$_2$Cl$_2$ (20 mL) was acidified with 4N HCl in dioxane. Hexane was added and the hydrochloride salt was collected by filtration and dried to give the title compound (50 mg, 2%). $^1$H NMR (DMSO-d$_6$) δ 7.45 (d, 2H), 7.30 (m, 5H), 6.72 (d, 2H), 5.22 (s, 1H), 3.62 (s, 3H). MS (ES+) m/z 408 (MH+).

EXAMPLE 9

Methyl N-{4-[2,2,2-trifluoro-1-hydroxy-1-(trifluoromethyl)ethyl]phenyl}-phenylalaninate

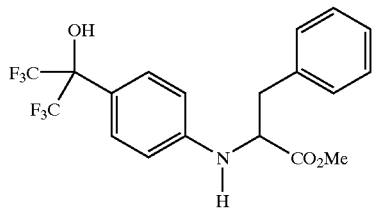

Step 1

3-Phenyl-2-({4-[2,2,2-trifluoro-1-hydroxy-1-(trifluoromethyl)ethyl]phenyl}-amino)propanenitrile To a mixture of phenylacetaldehyde (0.7 mL, 5.8 mmol) and trimethylsilyl cyanide 0.8 mL, 6.0 mmol) in $CH_2Cl_2$ (2 mL) was added 2-(4-aminophenyl)-1,1,1,3,3,3-hexafluoropropan-2-ol (Oakwood, 1.6 g, 6.1 mmol). The resulting mixture was stirred at ambient temperature over 18 h. The reaction mixture was diluted with $CH_2Cl_2$ and water. The organics were washed several times with water, dried ($MgSO_4$), and concentrated in vacuo. Purification by flash chromatography (8:1 hexanes/EtOAc) afforded the title compound as a pale yellow solid (1.4 g, 63%). MS (ES+) m/z 389 ($MH^+$).

Step 2

Methyl N-{4-[2,2,2-trifluoro-1-hydroxy-1-(trifluoromethyl)ethyl]phenyl}-phenylalaninate Sulfuric acid (1 mL) was added to the product of step 1 (1.4 g, 3.65 mmol) and the resulting mixture stirred at ambient temperature for 2.5 h. Methanol (2 mL) was added and the solution heated at reflux for 3 h. The solution was cooled to room temperature and 1 M NaOH added until a pH=8 was reached. The solution was extracted with ethyl acetate and the combined organics washed with brine, dried ($Na_2SO_4$) and concentrated in vacuo. Purification by reverse phase HPLC using a gradient elution of 60:40 $H_2O$/TFA:$CH_3CN$ to 0:100 $H_2O$/TFA:$CH_3CN$ at 254 nm afforded the title compound as a yellow oil (768 mg, 50%). $^1H$ NMR ($CDCl_3$) δ 7.47 (d, 2H), 7.32–7.25 (m, 3H), 7.14 (m, 2H), 6.61 (d, 2H), 4.38 (t, 1H), 3.70 (s, 3H), 3.25 (brs, 1H), 3.17 (dd, 1H), 3.11 (dd, 1H). MS (ES+) m/z 422 ($MH^+$). Anal. Calc. for $C_{19}H_{17}NO_3F_6+0.1H_2O$: C, 53.93; H, 4.10; N, 3.31. Found: C, 53.73; H, 3.92; N, 3.54.

EXAMPLE 10

Methyl(4-chlorophenyl)({4-[2,2,2-trifluoro-1-hydroxy-1-(trifluoromethyl)ethyl]-phenyl}amino)acetate

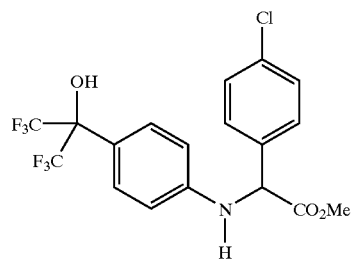

Prepared in the manner of Example 9 except 4-chlorobenzaldehyde was substituted for phenylacetaldehyde. Purification by reverse phase HPLC using a gradient elution of 60:40 $H_2O$/TFA:$CH_3CN$ to 0:100 $H_2O$/TFA:$CH_3CN$ at 254 nm afforded the title compound as a light yellow oil (4%). $^1H$ NMR ($CDCl_3$) δ 7.37 (m, 4H), 7.28 (m, 2H), 6.48 (d, 2H), 4.96 (s, 1H), 3.69 (s, 3H), 3.17 (brs, 1H). MS (ES+) m/z 442 ($MH^+$). Anal. Calc. for $C_{18}H_{14}NO_3F_6Cl$: C, 48.94; H, 3.19; N, 3.17. Found: C, 48.86; H, 3.01; N, 2.95.

EXAMPLE 11

Methyl(3,4-dichlorophenyl)({4-[2,2,2-trifluoro-1-hydroxy-1-(trifluoromethyl)ethyl]-phenyl}amino)acetate

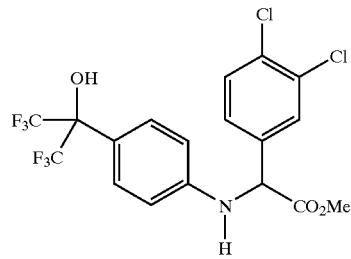

Prepared in the manner of Example 9 except 3,4-dichlorobenzaldehyde was substituted for phenylacetaldehyde. Purification by reverse phase HPLC using a gradient elution of 60:40 $H_2O$/TFA:$CH_3CN$ to 0:100 $H_2O$/TFA:$CH_3CN$ at 254 nm afforded the title compound as a colorless oil (22%). $^1H$ NMR ($CDCl_3$) δ 7.52 (d, 1H), 7.36 (m, 3H), 7.28 (dd, 1H), 6.49 (d, 2H), 4.92 (s, 1H), 3.69 (s, 3H), 3.18 (br s, 1H). MS (ES+) m/z 476 ($MH^+$). Anal. Calc. for $C_{18}H_{13}NO_3F_6Cl_2$: C, 45.40; H, 2.75; N, 2.94. Found: C, 45.19; H, 2.86; N, 2.66.

EXAMPLE 12

Methyl(4-methylphenyl)({4-[2,2,2-trifluoro-1-hydroxy-1-(trifluoromethyl)ethyl]-phenyl}amino)acetate

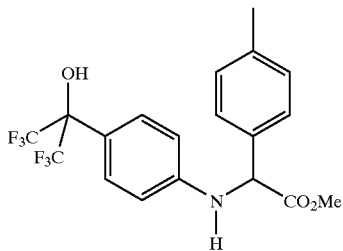

Prepared in the manner of Example 9 except p-tolualdehyde was substituted for phenylacetaldehyde. Purification by reverse phase HPLC using a gradient elution of 60:40 $H_2O$/TFA:$CH_3CN$ to 0:100 $H_2O$/TFA:$CH_3CN$ at 254 nm afforded the title compound as a white solid (68%). $^1$H NMR (CDCl$_3$) δ 7.35 (d, 2H), 7.29 (d, 2H), 7.10 (d, 2H), 6.52 (d, 2H), 4.94 (s, 1H), 3.66 (s, 3H), 3.15 (br s, 1H), 2.27 (s, 3H). MS (ES+) m/z 422 (MH$^+$). Anal. Calc. for $C_{19}H_{17}NO_3F_6$+0.1 TFA: C, 53.29; H, 3.98; N, 3.24. Found: C, 53.30; H, 4.16; N, 3.13.

EXAMPLE 13

2-(Methyl{4-[2,2,2-trifluoro-1-hydroxy-1-(trifluoromethyl)ethyl]phenyl}amino)ethyl propionate

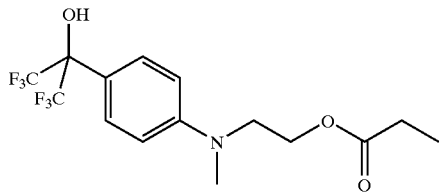

Step 1
2-[Methyl(phenyl)amino]ethyl propionate
To a solution of 2-[methyl(phenyl)amino]ethanol (500 mg, 3.3 mmol) in $CH_2Cl_2$ (17 mL) was added triethylamine (1.4 mL, 9.9 mmol) followed by propionyl chloride (0.4 mL, 5.0 mmol). After stirring at ambient temperature over 18 hours, the reaction mixture was diluted with EtOAc and washed several times with brine. The organic layer was dried ($Na_2SO_4$) and concentrated to afford the title compound (700 mg, quantitative yield). MS (ES+) m/z 208 (MH$^+$).
Step 2
2-(Methyl{4-[2,2,2-trifluoro-1-hydroxy-1-(trifluoromethyl)ethyl]phenyl}amino)ethyl propionate
Prepared in the manner of Example 1 step 1 except 2-[methyl(phenyl)-amino]ethyl propionate was substituted for aniline. Purification by flash chromatography (2:1 hexanes/EtOAc) afforded the title compound as white solid (48%). $^1$H NMR (CDCl$_3$) δ 7.44 (d, 2H), 7.19 (s, 1H), 6.68 (d, 2H), 4.20 (t, 2H), 3.57 (t, 2H), 2.94 (s, 3H), 2.17 (q, 2H), 1.00 (t, 3H). Anal. Calc. for $C_{15}H_{17}F_6NO_3$: C, 48.26; H, 4.59; N, 3.75. Found: C, 48.18; H, 4.64; N, 3.78. HRMS (MH$^+$). Calc.: 374.1191. Found: 374.1196.

EXAMPLE 14

Ethyl N-methyl-N-{4-[2,2,2-trifluoro-1-hydroxy-1-(trifluoromethyl)ethyl]phenyl}-beta-alaninate

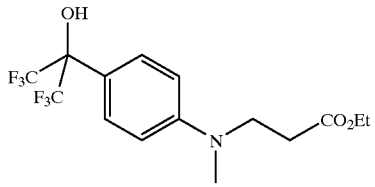

Step 1
1,1,1,3,3,3-Hexafluoro-2-[4-(methylamino)phenyl]propan-2-ol
Prepared in the manner of Example 1 step 1 except N-methylaniline was substituted for aniline. Purification by flash chromatography (4:1 hexanes/EtOAc) afforded the title compound as a yellow solid (85%). MS (ES+) m/z 274 (MH$^+$).
Step 2
Ethyl N-methyl-N-{4-[2,2,2-trifluoro-1-hydroxy-1-(trifluoromethyl)ethyl]phenyl}-beta-alaninate
To the product of step 1 (1.26 g, 4.6 mmol) was added ethyl acrylate (0.55 mL, 5.1 mL) and glacial acetic acid (0.02 mL, 0.3 mmol). After heating the reaction mixture at reflux over 18 h, the solution was cooled to room temperature and diluted with ethyl acetate. The organics were washed several times with water, dried ($Na_2SO_4$), and concentrated in vacuo. Purification by reverse phase HPLC using a gradient elution of 60:40 $H_2O$/TFA:$CH_3CN$ to 0:100 $H_2O$/TFA:$CH_3CN$ at 254 nm afforded the title compound as a white solid (1.25 g, 73%): mp=77° C. $^1$H NMR (CDCl$_3$) δ 7.49 (d, 2H), 6.78 (d, 2H), 4.06 (q, 2H), 3.63 (t, 2H), 3.26 (br s, 1H), 2.92 (s, 3H), 2.54 (t, 2H), 1.14 (t, 3H). MS (ES+) m/z 374 (MH$^+$). Anal. Calc. for $C_{15}H_{17}NO_3F_6$: C, 48.26; H, 4.59; N, 3.75. Found: C, 47.95; H, 4.67; N, 3.73.

EXAMPLE 15

Ethyl N-(2-methoxyethyl)-N-{4-[2,2,2-trifluoro-1-hydroxy-1-(trifluoromethyl)ethyl]phenyl}glycinate

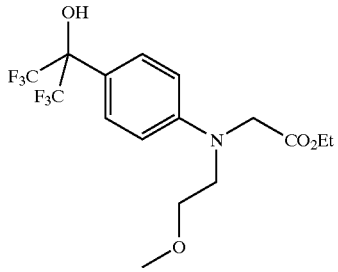

Prepared in the manner of Example 2 steps 2 and 3 except 2-bromoethyl methyl ether was substituted for iodomethane and cat. NaI was added to the reaction mixture. Purification by reverse phase HPLC using a gradient elution of 60:40 $H_2O$/TFA:$CH_3CN$ to 0:100 $H_2O$/TFA:$CH_3CN$ at 254 nm afforded the title compound as green oil (30%). $^1$H NMR (CDCl$_3$) δ 7.43 (d, 2H), 6.62 (d, 2H), 4.12 (q, 2H), 4.06 (s, 2H), 3.56 (br s, 4H), 3.28 (s, 3H), 1.20 (t, 3H). Anal. Calc. for $C_{16}H_{19}NO_4F_6$+0.2$H_2O$: C, 47.23; H, 4.81; N, 3.44. Found: C, 47.26; H, 5.04; N, 3.45. HRMS (MH$^+$). Calc.: 404.1297. Found: 404.1312.

EXAMPLE 16

Ethyl N-(4-chlorobenzyl)-N-{4-[2,2,2-trifluoro-1-hydroxy-1-(trifluoromethyl)ethyl]-phenyl}glycinate

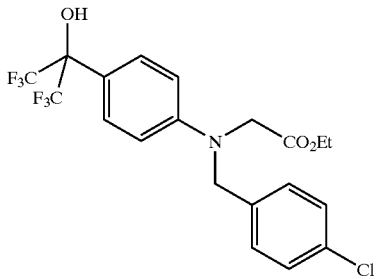

Step 1
Ethyl N-(4-chlorobenzyl)-N-phenylglycinate

N-phenylglycine ethyl ester (781 mg, 4.3 mmol), 4-chlorobenzyl chloride (690 mg, 4.3 mmol) and sodium iodide (64 mg) were dissolved in toluene (7 mL) under argon. The reaction was heated in a graphite bath at 80° C. for 24 h. After cooling to room temperature, the reaction was diluted with ethyl acetate and washed with 1M HCl followed by brine. The solution was dried over $MgSO_4$, filtered, and concentrated in vacuo. Purification of the resultant oil by flash chromatography (10:1 hexanes/EtOAc) afforded the title compound as a green oil (669 mg, 51%). MS (ES+) m/z 304 ($MH^+$).

Step 2
Ethyl N-(4-chlorobenzyl)-N-{4-[2,2,2-trifluoro-1-hydroxy-1-(trifluoromethyl)ethyl]-phenyl}glycinate Prepared in the manner of Example 1 step 1 except ethyl N-(4-chlorobenzyl)-N-phenylglycinate was substituted for aniline. Purification by flash chromatography (5:1 hexanes/EtOAc) afforded the title compound as a yellow oil (19%). $^1$H NMR ($CDCl_3$) δ 7.42 (d, 2H), 7.24 (d, 2H), 7.15 (d, 2H), 6.59 (d, 2H), 4.56 (s, 2H), 4.15 (q, 2H), 4.02 (s, 2H), 1.20 (t, 3H). Anal. Calc. for $C_{20}H_{18}NO_3F_6Cl+0.4H_2O$: C, 50.36; H, 3.97; N, 2.94. Found: C, 50.49; H, 4.31; N, 2.80. HRMS ($MH^+$) Calc.: 470.0958. Found: 470.0980.

EXAMPLE 17

Ethyl N-(3,4-dichlorobenzyl)-N-{4-[2,2,2-trifluoro-1-hydroxy-1-(trifluoromethyl)ethyl]phenyl}glycinate

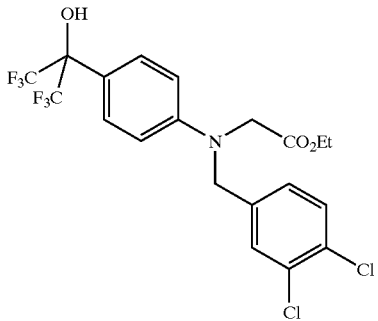

Prepared in the manner of Example 16 except 3,4-dichlorobenzyl chloride was substituted for 4-chlorobenzyl chloride. Purification by reverse phase HPLC using a gradient elution of 60:40 $H_2O$/TFA:$CH_3CN$ to 0:100 $H_2O$/TFA:$CH_3CN$ at 254 nm afforded the title compound as a colorless oil (31%). $^1$H NMR ($CDCl_3$) δ 7.54 (d, 2H), 7.42 (m, 2H), 7.16 (dd, 1H), 6.67 (d, 2H), 4.63 (s, 2H), 4.25 (q, 2H), 4.12 (s, 2H), 1.30 (t, 3H). Anal. Calc. for $C_{20}H_{17}NO_3F_6Cl_2+0.4H_2O$: C, 46.97; H, 3.51; N, 2.74. Found: C, 46.92; H, 3.80; N, 2.57. HRMS ($MH^+$) Calc.: 504.0568. Found: 504.0586.

EXAMPLE 18

Ethyl N-(4-methylbenzyl)-N-{4-[2,2,2-trifluoro-1-hydroxy-1-(trifluoromethyl)ethyl]-phenyl}glycinate

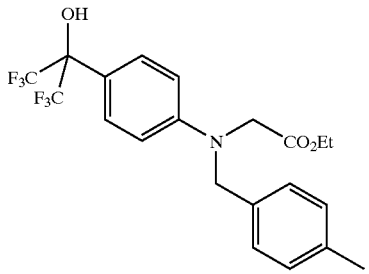

Prepared in the manner of Example 16 except 4-methylbenzyl chloride was substituted for 4-chlorobenzyl chloride. Purification by reverse phase HPLC using a gradient elution of 60:40 $H_2O$/TFA:$CH_3CN$ to 0:100 $H_2O$/TFA:$CH_3CN$ at 254 nm afforded the title compound as a yellow oil (2%).

$^1$H NMR ($CDCl_3$) δ 7.47 (d, 2H), 7.15 (s, 4H), 6.70 (d, 2H), 4.62 (s, 2H), 4.21 (q, 2H), 4.07 (s, 2H), 2.33 (s, 3H), 1.26 (t, 3H). MS (ES+) m/z 450 ($MH^+$).

EXAMPLE 19

Ethyl N-benzyl-N-{4-[2,2,2-trifluoro-1-hydroxy-1-(trifluoromethyl)ethyl]-phenyl}glycinate

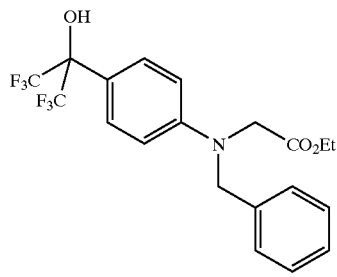

Prepared in the manner of Example 16 except benzyl bromide was substituted for 4-chlorobenzyl chloride. Purification by reverse phase HPLC using a gradient elution of 60:40 $H_2O$/TFA:$CH_3CN$ to 0:100 $H_2O$/TFA:$CH_3CN$ at 254 nm afforded the title compound as a white solid (42%): mp=116° C.

$^1$H NMR ($CDCl_3$) δ 7.51 (d, 2H), 7.48–7.33 (m, 2H), 7.31–7.26 (m, 3H), 6.73 (d, 2H), 4.69 (s, 2H), 4.24 (q, 2H), 4.12 (s, 2H), 3.29 (br s, 1H), 1.29 (t, 3H). MS (ES+) m/z 436 ($MH^+$). Anal. Calc. for $C_{20}H_{19}NO_3F_6$: C, 55.18; H, 4.40; N, 3.22. Found: C, 54.79; H, 4.22; N, 3.12.

EXAMPLE 20

N-Methyl-N-{4-[2,2,2-trifluoro-1-hydroxy-1-(trifluoromethyl)ethyl]phenyl}glycine

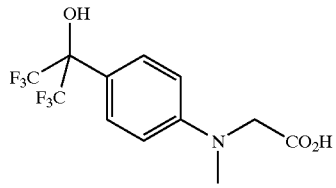

Example 7 (162 mg, 0.45 mmol) was dissolved in THF (5 mL) and 1M LiOH (2.5 mL) added. The reaction was stirred vigorously over 18 h. After the addition of 1M HCl (2.5 mL), the reaction was concentrated in vacuo. Purification by reverse phase HPLC using a gradient elution of 60:40 $H_2O$/TFA:$CH_3CN$ to 0:100 $H_2O$/TFA:$CH_3CN$ at 254 nm afforded the title compound as a yellow oil (70%). $^1H$ NMR (CDCl$_3$) δ 7.44 (d, 2H), 6.78 (d, 2H), 3.94 (br s, 3H), 2.94 (s, 3H). MS (ES+) m/z 332 (MH$^+$). Anal. Calc. for $C_{12}H_{11}NO_3F_6$+1.3 TFA+1$H_2O$: C, 35.25; H, 2.90; N, 2.82. Found: C, 35.14; H, 3.01; N, 2.77.

EXAMPLE 21

Ethyl N-(2-chlorobenzyl)-N-{4-[2,2,2-trifluoro-1-hydroxy-1-(trifluoromethyl)ethyl]phenyl}glycinate

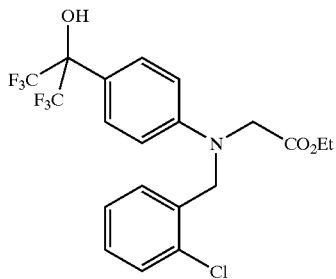

Prepared in the manner of Example 2 steps 2 and 3 except 2-chlorobenzyl bromide was substituted for iodomethane and cat. NaI was added to the reaction mixture. Purification by flash chromatography (6:1 hexanes/EtOAc) afforded the title compound as a yellow solid (38%): mp=146° C. $^1H$ NMR (CDCl$_3$) δ 7.52 (d, 2H), 7.43 (m, 1H), 7.23 (m, 3H), 6.64 (d, 2H), 4.73 (s, 2H), 4.26 (q, 2H), 4.15 (s, 2H), 1.30 (t, 3H). Anal. Calc. for $C_{20}H_{18}NO_3F_6Cl$+0.3$H_2O$: C, 50.55; H, 3.95; N, 2.95. Found: C, 50.62; H, 4.08; N, 2.98. HRMS (MH$^+$). Calc.: 470.0958. Found: 470.0970.

EXAMPLE 22

Ethyl N-(pyridin-3-ylmethyl)-N-{4-[2,2,2-trifluoro-1-hydroxy-1-(trifluoromethyl)ethyl]phenyl}glycinate

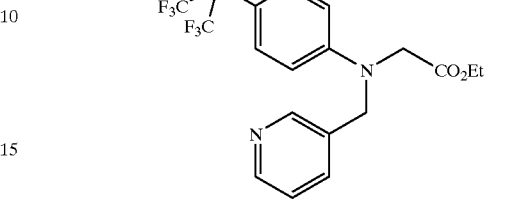

Prepared in the manner of Example 2 steps 2 and 3 except 3-(bromomethyl)pyridine was substituted for iodomethane and cat. NaI was added to the reaction mixture. Purification by flash chromatography (1:1 hexanes/EtOAc) afforded the title compound as a yellow solid (73%): mp=55° C. $^1H$ NMR (CDCl$_3$) δ 8.55 (br s, 1H), 8.50 (d, 1H), 7.86 (br d, 1H), 7.58 (d, 2H), 7.42 (m, 1H), 6.68 (d, 2H), 4.72 (s, 2H), 4.25 (q, 2H), 4.15 (s, 2H), 1.28 (t, 3H). Anal. Calc. for $C_{19}H_{18}N_2O_3F_6$: C, 52.30; H, 4.16; N, 6.42. Found: C, 52.32; H, 4.27; N, 6.40. HRMS (MH$^+$). Calc.: 437.1300. Found: 437.1316.

EXAMPLE 23

1,1,1,3,3,3-Hexafluoro-2-{4-[(2-hydroxyethyl)(methyl)amino]phenyl}propan-2-ol

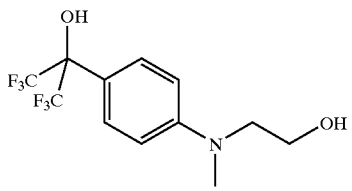

Ethyl N-methyl-N-{4-[2,2,2-trifluoro-1-hydroxy-1-(trifluoromethyl)ethyl]phenyl}-glycinate (272 mg, 0.76 mmol) was dissolved in anhydrous THF(5 mL) under argon and 1M lithium aluminum hydride solution in THF (1.1 mL, 1.1 mmol) was added. The resulting solution was stirred at ambient temperature over 18 h. The reaction was quenched slowly with ethyl acetate then diluted with $H_2O$. The layers were separated and the organic phase was washed with water followed by brine. The organics were dried over MgSO$_4$, filtered and concentrated in vacuo. The resultant oil was purified by flash chromatography (4:1 hexanes/EtOAc) to afford the title compound as a yellow oil (176 mg, 73%). $^1H$ NMR (CDCl$_3$) δ 7.56 (d, 2H), 6.86 (d, 2H), 3.86 (t, 2H), 3.55 (t, 2H), 3.06 (s, 3H). Anal. Calc. for $C_{12}H_{13}NO_2F_6$+0.1$H_2O$: C, 45.18; H, 4.17; N, 4.39. Found: C, 45.01; H, 4.05; N, 4.28. HRMS (MH$^+$) Calc.: 318.0918. Found: 318.0929.

EXAMPLE 24

2-{4-[(2-Ethoxyethyl)(methyl)amino]phenyl}-1,1,1,3,3,3-hexafluoropropan-2-ol

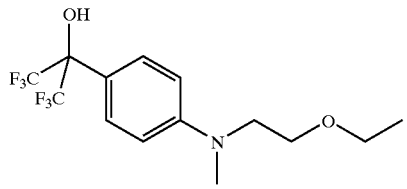

Step 1
2-[Methyl(phenyl)amino]ethanol

Prepared in the manner of Example 23 except ethyl N-methyl-N-phenylglycinate was substituted for ethyl N-methyl-N-{4-[2,2,2-trifluoro-1-hydroxy-1-(trifluoromethyl)ethyl]phenyl}glycinate. Purification by flash chromatography (1:1 hexanes/EtOAc) afforded the title compound as a yellow oil (89%). MS (ES+) m/z 152 (MH$^+$).

Step 2
N-(2-ethoxyethyl)-N-methyl-N-phenylamine

To a solution of the product from step 1 (850 mg, 506 mmol) in DMSO (4 mL) and KOH (1.2 g, 22.0 mmol) was added ethyl bromide (0.85 mL, 11.4 mmol). After stirring 1.5 hours at ambient temperature, the reaction mixture was diluted with water and the product extracted with $CH_2Cl_2$ (3×). The combined organic layers were dried ($MgSO_4$), filtered and concentrated to afford the title compound as a yellow oil (950 mg, 95%). MS (ES+) m/z 180 (MH$^+$).

Step 3
2-{4-[(2-Ethoxyethyl)(methyl)amino]phenyl}-1,1,1,3,3,3-hexafluoropropan-2-ol Prepared in the manner of Example 1 step 1 except N-(2-ethoxyethyl)-N-methyl-N-phenylamine was substituted for aniline. Purification by flash chromatography (8:1 hexanes/EtOAc) afforded the title compound as a yellow oil (18%). $^1$H NMR (CDCl$_3$) δ 7.68 (d, 2H), 6.95 (d, 2H), 3.73 (m, 4H), 3.72 (q, 2H), 3.18 (s, 3H), 1.32 (t, 2H). Anal. Calc. for $C_{14}H_{17}NO_2F_6$+0.2 TFA: C, 46.99; H, 4.71; N, 3.81. Found: C, 47.26; H, 4.92; N, 3.77. HRMS (MH$^+$). Calc.: 346.1242. Found: 346.1235.

EXAMPLE 25

2-(Methyl{4-[2,2,2-trifluoro-1-hydroxy-1-(trifluoromethyl)ethyl]phenyl}amino)-propan-1-ol

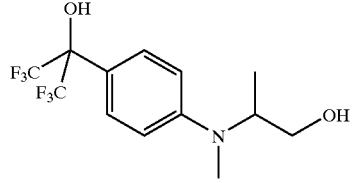

Prepared in the manner of Example 23 except ethyl N-methyl-N-{4-[2,2,2-trifluoro-1-hydroxy-1-(trifluoromethyl)ethyl]phenyl}alaninate was substituted for ethyl N-methyl-N-{4-[2,2,2-trifluoro-1-hydroxy-1-(trifluoromethyl)ethyl]phenyl}-glycinate. Purification by flash chromatography (4:1 hexanes/EtOAc) afforded the title compound as a pink oil (84%). $^1$H NMR (CDCl$_3$) δ 7.48 (d, 2H), 6.86 (br d, 2H), 4.04 (m, 1H), 3.56 (m, 2H), 2.72 (s, 3H), 1.03 (d, 3H). Anal. Calc. $C_{13}H_{15}NO_2F_6$: C, 47.14; H, 4.56; N, 4.23. Found: C, 46.89; H, 4.61; N, 3.93. HRMS (MH$^+$) Calc.: 332.1085. Found: 332.1073.

EXAMPLE 26

N-1-Benzyl-N-2-{4-[2,2,2-trifluoro-1-hydroxy-1-(trifluoromethyl)ethyl]phenyl}alaninamide

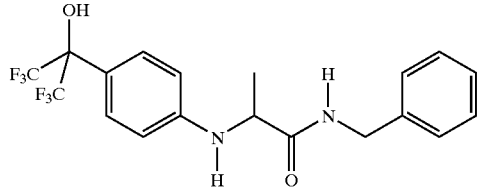

N-{4-[2,2,2-Trifluoro-1-hydroxy-1-(trifluoromethyl)ethyl]phenyl}alanine (164 mg, 045 mmol), benzyl amine (0.05 mL, 0.46 mmol), bromotrispyrrolidinophosphonium hexafluorophosphate (PyBroP, 222 mg, 0.47 mmol), and N,N-diisopropylethylamine (0.25 mL, 1.4 mmol) were combined in $CH_2Cl_2$ (5 mL) under argon and stirred over 18 h at ambient temperature. The reaction was diluted with $CH_2Cl_2$ and washed with saturated NaHCO$_3$ followed by brine. The solution was dried over MgSO$_4$, filtered, and concentrated in vacuo. The resultant oil was purified by flash chromatography (2:1 hexanes/EtOAc) to afford the title compound as a yellow waxy solid (53 mg, 28%). $^1$H NMR (CDCl$_3$) δ 7.45 (d, 2H), 7.17 (m, 3H), 7.07 (m, 2H), 6.57 (d, 2H), 4.36 (t, 2H), 3.81 (q, 1H), 1.48 (d, 3H). Anal. Calc. for $C_{19}H_{18}N_2O_2F_6$+0.2H$_2$O: C, 53.83; H, 4.37; N, 6.61. Found: C, 53.82; H, 4.35; N, 6.54. HRMS (MH$^+$) Calc.: 421.1351. Found: 421.1374.

EXAMPLE 27

Ethyl 1-({4-[2,2,2-trifluoro-1-hydroxy-1-(trifluoromethyl)ethyl]phenyl}amino)-cyclopentanecarboxylate

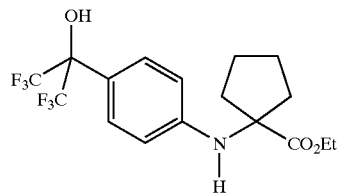

Prepared in the manner of Example 4 except ethyl 1-aminocyclopentane-carboxylate was substituted for ethyl pipecolinate. Purification by reverse phase HPLC using a gradient elution of 60:40 H$_2$O/TFA:CH$_3$CN to 0:100 H$_2$O/TFA:CH$_3$CN at 254 nm afforded the title compound as a colorless film (9%). $^1$H NMR (CDCl$_3$) δ 7.41 (d, 2H), 6.68 (d, 2H), 4.07 (q, 2H), 2.31–2.22 (m, 2H), 1.98–1.92 (m, 2H), 1.83–1.68 (m, 4H), 1.04 (t, 3H). Anal. Calc. for $C_{17}H_{19}NO_3F_6$: C, 51.13; H, 4.80; N, 3.51. Found: C, 50.87; H, 4.95; N, 3.38. HRMS (MH$^+$) Calc.: 400.1365. Found: 400.1360.

EXAMPLE 28

Ethyl 1-({4-[2,2,2-trifluoro-1-hydroxy-1-(trifluoromethyl)ethyl]phenyl}amino)-cyclohexanecarboxylate

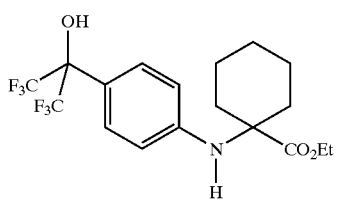

Prepared in the manner of Example 9 except cyclohexanone was substituted for phenylacetaldehyde. Purification by flash chromatography (6:1 hexanes/EtOAc) afforded the title compound as a white semi-solid (72%). $^1$H NMR (CDCl$_3$) δ 7.55 (d, 2H), 6.83 (d, 2H), 4.24 (q, 2H), 2.18–2.07 (m, 4H), 1.73–1.62 (m, 6H), 1.24 (t, 3H). Anal. Calc. for C$_{18}$H$_{21}$NO$_3$F$_6$: C, 52.30; H, 5.12; N, 3.39. Found: C, 52.19; H, 5.52; N, 3.35. HRMS (MH$^+$) Calc.: 414.1531. Found: 414.1519.

EXAMPLE 29

N~1~-Benzyl-N~2~-methyl-N~2~-{4-[2,2,2-trifluoro-1-hydroxy-1-(trifluoromethyl)ethyl]phenyl}glycinamide

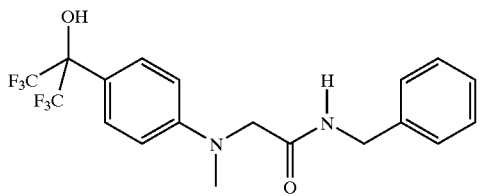

Prepared in the manner of Example 26 except N-methyl-N-{4-[2,2,2-trifluoro-1-hydroxy-1-(trifluoromethyl)ethyl]phenyl}glycine was substituted for N-{4-[2,2,2-trifluoro-1-hydroxy-1-(trifluoromethyl)ethyl]phenyl}alanine. Purification by reverse phase HPLC using a gradient elution of 80:20 H$_2$O/TFA:CH$_3$CN to 20:80 H$_2$O/TFA:CH$_3$CN at 254 nm afforded the title compound as a white powder (65%). $^1$H NMR (CDCl$_3$) δ 7.57 (d, 2H), 7.28 (m, 2H), 7.16 (m, 2H), 6.74 (d, 2H), 6.70 (m, 1H), 4.49 (d, 2H), 3.97 (s, 2H), 3.05 (s, 3H). Anal. Calc. for C$_{19}$H$_{18}$N$_2$O$_2$F$_6$: C, 54.29; H, 4.32; N, 6.66. Found: C, 53.96; H, 4.51; N, 6.57. HRMS (MH$^+$) Calc.: 421.1391. Found: 421.1377.

EXAMPLE 30

N~1~-Benzyl-N~3~-methyl-N~3~-{4-[2,2,2-trifluoro-1-hydroxy-1-(trifluoromethyl)ethyl]phenyl}-beta-alaninamide

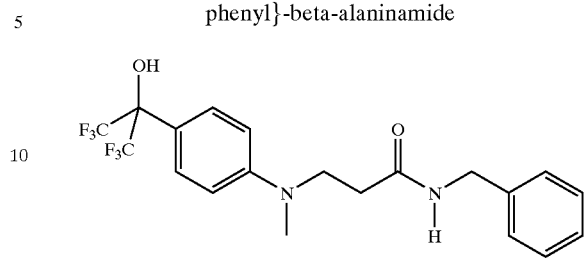

Step 1
N-Methyl-N-{4-[2,2,2-trifluoro-1-hydroxy-1-(trifluoromethyl)ethyl]phenyl}-beta-alanine
Prepared in the manner of Example 20 step 3 except ethyl N-methyl-N-{4-[2,2,2-trifluoro-1-hydroxy-1-(trifluoromethyl)ethyl]phenyl}-beta-alaninate was substituted for ethyl N-{2-methyl-4-[2,2,2-trifluoro-1-hydroxy-1-(trifluoromethyl)ethyl]-phenyl}alaninate. Purification by reverse phase HPLC using a gradient elution of 80:20 H$_2$O/TFA:CH$_3$CN to 20:80 H$_2$O/TFA:CH$_3$CN at 254 nm afforded the title compound as a white solid (99%). MS (ES+) m/z 346 (MH$^+$).

Step 2
N~1~-Benzyl-N~3~-methyl-N~3~-{4-[2,2,2-trifluoro-1-hydroxy-1-(trifluoromethyl)ethyl]phenyl}-beta-alaninamide
Prepared in the manner of Example 26 except N-methyl-N-{4-[2,2,2-trifluoro-1-hydroxy-1-(trifluoromethyl)ethyl]phenyl}-beta-alanine was substituted for N-{4-[2,2,2-trifluoro-1-hydroxy-1-(trifluoromethyl)ethyl]phenyl}alanine. Purification by reverse phase HPLC using a gradient elution of 60:40 H$_2$O/TFA:CH$_3$CN to 0:100 H$_2$O/TFA:CH$_3$CN at 254 nm afforded the title compound as a white powder (60%). $^1$H NMR (CDCl$_3$) δ 7.90 (d, 2H), 7.49–7.41 (m, 5H), 7.37 (d, 2H), 6.63 (m, 1H), 4.51 (d, 2H), 3.98 (t, 2H), 3.22 (s, 3H), 2.84 (t, 2H). Anal. Calc. for C$_{20}$H$_{20}$N$_2$O$_2$F$_6$: C, 55.30; H, 4.64; N, 6.45. Found: C, 55.04; H, 4.76; N, 6.50. HRMS (MH$^+$) Calc.: 435.1524. Found: 435.1520.

EXAMPLE 31

Ethyl [6-[2,2,2-trifluoro-1-hydroxy-1-(trifluoromethyl)ethyl]-3,4-dihydroquinolin-1(2H)-yl]acetate

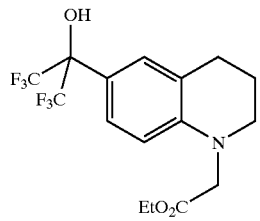

Step 1
1,1,1,3,3,3-Hexafluoro-2-(1,2,3,4-tetrahydroquinolin-6-yl)propan-2-ol
Prepared in the manner of Example 1 step 1 except 1,2,3,4-tetrahydroquinoline was substituted for aniline. Purification by flash chromatography (6:1 hexanes/EtOAc) afforded the title compound as a white solid (78%). MS (ES+) m/z 300 (MH$^+$).

Step 2
Ethyl [6-[2,2,2-trifluoro-1-hydroxy-1-(trifluoromethyl)ethyl]-3,4-dihydroquinolin-1(2H)-yl]acetate Prepared in the manner of Example 5 steps 2–4 except 1,1,1,3,3,3-hexafluoro-2-(1,2,3,4-tetrahydroquinolin-6yl)propan-2-ol was substituted for 1,1,1,3,3,3-hexafluoro-2-{4-[(2,2,2-trifluoroethyl)amino]phenyl}propan-2-ol. Purification by reverse phase HPLC using a gradient elution of 60:40 H$_2$O/TFA:CH$_3$CN to 0:100 H$_2$O/TFA:CH$_3$CN at 254 nm afforded the title compound as a white solid (42%): mp=66.5° C. $^1$H NMR (CDCl$_3$) δ 7.22 (m, 1H), 7.17 (s, 1H), 6.34 (d, 1H), 4.12 (q, 2H), 3.93 (s, 2H), 3.36 (t, 2H), 2.72 (t, 2H), 1.94 (m, 2H), 1.19 (t, 3H). MS (ES+) m/z 386 (MH$^+$). Anal. Calc. for C$_{16}$H$_{17}$NO$_3$F$_6$: C, 49.88; H, 4.45; N, 3.64. Found: C, 49.81; H, 4.62; N, 3.51. HRMS (MH$^+$) Calc.: 386.1191. Found: 386.1208.

EXAMPLE 32

N~1~-Methoxy-N~1~-N~2~-dimethyl-N~2~-{4-[2,2,2-trifluoro-1-hydroxy-1-(trifluoromethyl)ethyl]phenyl}glycinamide

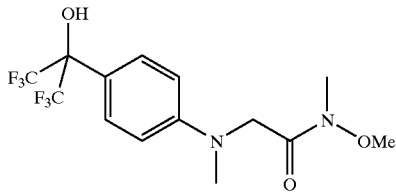

Prepared in the manner of Example 26 except N-methyl-N-{4-[2,2,2-trifluoro-1-hydroxy-1-(trifluoromethyl)ethyl]phenyl}glycine was substituted for N-{4-[2,2,2-trifluoro-1-hydroxy-1-(trifluoromethyl)ethyl]phenyl}alanine and N,O-dimethylhydroxylamine was substituted for benzyl amine. Purification by flash chromatography (4:1 EtOAc/hexanes) afforded the title compound as a white solid (96%): mp=121° C. $^1$H NMR (CDCl$_3$) δ 7.50 (d, 2H), 6.69 (d, 2H), 4.28 (s, 2H), 3.78 (s, 3H), 3.21 (s, 3H), 3.09 (s, 3H). $^{13}$C NMR (CDCl$_3$) δ 172.7, 150.3, 127.5, 116.9, 111.6, 61.5, 53.0, 39.5. MS (ES+) m/z 375 (MH$^+$).

EXAMPLE 33

1-(Methyl{4-[2,2,2-trifluoro-1-hydroxy-1-(trifluoromethyl)ethyl]phenyl}amino)-pentan-2-one

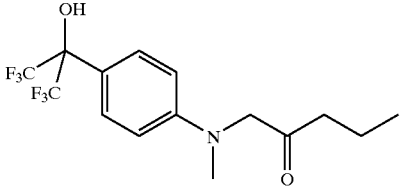

To a solution of N~1~-methoxy-N~1~-N~2~-dimethyl-N~2~-{4-[2,2,2-trifluoro-1-hydroxy-1-(trifluoromethyl)ethyl]phenyl}glycinamide (240 mg, 0.64 mmol) in CH$_2$Cl$_2$ (3.5 mL) at 0° C. under a nitrogen atmosphere was slowly added a solution of propylmagnesium chloride (1.6 mL, 2M in Et$_2$O). After stirring 3 hours, the reaction mixture was poured into 1M HCl and extracted twice with EtOAc. The organic layer was washed with brine, dried (Na$_2$SO$_4$), filtered, and concentrated. Purification by flash chromatography (2:1 EtOAc/hexanes) afforded the title compound as a dark yellow waxy solid (110 mg, 48%). $^1$H NMR (CDCl$_3$) δ 7.51 (d, 2H), 6.62 (d, 2H), 4.07 (s, 2H), 3.09 (s, 3H), 2.41 (t, 2H), 1.64 (q, 3H), 0.92 (t, 3H). $^{13}$C NMR (CDCl$_3$) δ 209.0, 149.8, 127.6, 117.0, 111.4, 62.2, 41.5, 39.6, 16.9, 13.7. MS (ES+) m/z 358 (MH$^+$).

EXAMPLE 34

1-(Methyl{4-[2,2,2-trifluoro-1-hydroxy-1-(trifluoromethyl)ethyl]phenyl}amino)-pentan-2-ol

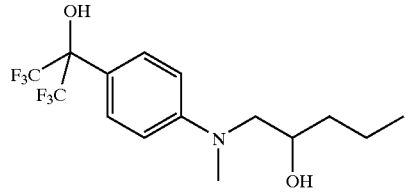

To a solution of 1-(methyl{4-[2,2,2-trifluoro-1-hydroxy-1-(trifluoromethyl)-ethyl]phenyl}amino)-pentan-2-one (52 mg, 0.15 mmol) in methanol (3 mL) at −78° C. was added sodium borohydride (17 mg, 0.44 mmol). The reaction mixture was allowed to warm to ambient temperature over 4 hours. The reaction mixture was quenched with water and extracted twice with EtOAc. The combined organic layers were washed with brine, dried (Na$_2$SO$_4$), filtered and concentrated. Purification by flash chromatography (4:1 hexanes/EtOAc) afforded the title compound as a colorless oil (40 mg, 74%). $^1$H NMR (CDCl$_3$) δ 7.51 (d, 2H), 6.80 (d, 2H), 3.96 (m, 1H), 3.32 (s, 1H), 3.30 (dq, 2H), 3.03 (s, 3H), 1.39–1.52 (m, 4H), 0.96 (t, 3H). $^{13}$C NMR (CDCl$_3$) δ 151.0, 127.4, 116.8, 112.1, 69.4, 60.0, 39.3, 36.8, 18.9, 14.1. MS (ES+) m/z 360 (MH$^+$).

EXAMPLE 35

4-Chlorobenzyl N-methyl-N-{4-[2,2,2-trifluoro-1-hydroxy-1-(trifluoromethyl)-ethyl]phenyl}glycinate

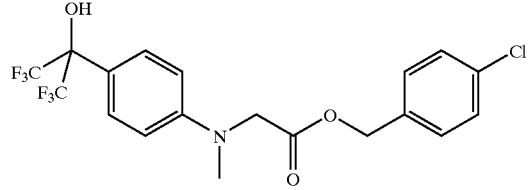

Step 1
Ethyl N-methyl-N-phenylglycinate

Ethyl N-Phenylglycinate (2 g, 11.1 mmol) was dissolved in toluene (4.5 mL) and iodomethane (0.35 mL, 5.6 mmol) added. After warming at 70° C. over 4 hours, the reaction mixture was cooled to ambient temperature and diluted with EtOAc. The organic layer was washed several times with brine, dried (Na$_2$SO$_4$), filtered, and concentrated. Purification by flash chromatography (10:1 hexanes/EtOAc) afforded a quantitative yield of the title compound as a light yellow oil. MS (ES+) m/z 194 (MH$^+$).

Step 2
N-Methyl-N-phenylglycine

The product of step 1 (1.1 g, 5.6 mmol) was dissolved in methanol (50 mL) and 1M NaOH (17 mL) added. Allow reaction mixture to stir at ambient temperature over 18 hours. 10% Citric acid solution was added until a pH=4 was reached. Extract several times with EtOAc. The organic layer was washed several times with brine, dried (Na₂SO₄), filtered, and concentrated affording a quantitative yield of the title compound as a yellow oil. MS (ES+) m/z 166 (MH⁺).

Step 3

4-Chlorobenzyl N-methyl-N-phenylglycinate

The product from step 2 (220 mg, 1.3 mmol) was dissolved in DMF (7 mL) and Cs₂CO₃ (652 mg, 2.0 mmol) added, followed by 4-chlorobenzyl chloride (214 mg, 1.3 mmol). Allow reaction mixture to stir at ambient temperature over 18 hours. The reaction mixture was diluted with EtOAc and washed several times with brine. The organic layer was dried (Na₂SO₄), filtered and concentrated to afford the title compound as a yellow oil (68%). MS (ES+) m/z 290 (MH⁺).

Step 4

4-Chlorobenzyl N-methyl-N-{4-[2,2,2-trifluoro-1-hydroxy-1-(trifluoromethyl)-ethyl]phenyl}glycinate Prepared in the manner of Example 1 step 1 except 4-chlorobenzyl N-methyl-N-phenylglycinate was substituted for aniline. Purification by reverse phase HPLC using a gradient elution of 60:40 H₂O/TFA:CH₃CN to 0:100 H₂O/TFA:CH₃CN at 254 nm afforded the title compound as a colorless oil (12%): mp=66.5° C. ¹H NMR (CDCl₃) δ 7.52 (d, 2H), 7.29 (d, 2H), 7.17 (d, 2H), 6.68 (d, 2H), 5.11 (s, 2H), 4.13 (s, 2H), 3.08 (s, 3H). ¹³C NMR (CDCl₃) δ 170.4, 149.7, 134.4, 133.8, 129.6, 128.8, 127.5, 117.4, 111.8, 66.0, 54.2, 39. MS (ES+) m/z456 (MH⁺). HRMS (MH⁺) Calc.: 456.0814. Found: 456.0818.

EXAMPLE 36

2-Ethoxyethyl N-methyl-N-{4-[2,2,2-trifluoro-1-hydroxy-1-(trifluoromethyl)ethyl]-phenyl}glycinate

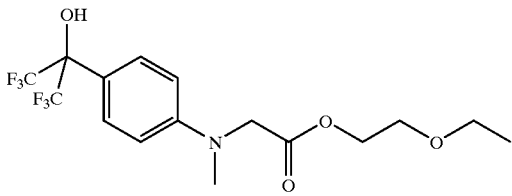

Prepared in the manner of Example 35 except 2-bromoethyl ethyl ether was substituted for 4-chlorobenzyl chloride. Purification by reverse phase HPLC using a gradient elution of 60:40 H₂O/TFA:CH₃CN to 0:100 H₂O/TFA:CH₃CN at 254 nm afforded the title compound as a yellow oil (51%).

¹H NMR (CDCl₃) δ 7.45 (d, 2H), 6.67 (d, 2H), 4.22 (dt, 2H), 4.07 (s, 2H), 3.54 (dt, 2H), 3.43 (q, 2H), 3.05 (s, 3H), 1.12 (t, 3H). MS (ES+) m/z404 (MH⁺). Anal. Calc. for C₁₆H₁₉NO₄F₆: C, 47.65; H, 4.75; N, 3.47. Found: C, 47.36; H, 4.74; N, 3.45. HRMS (MH⁺) Calc.: 404.1313. Found: 404.1316.

EXAMPLE 37

2-Methoxyethyl N-methyl-N-{4-[2,2,2-trifluoro-1-hydroxy-1-(trifluoromethyl)ethyl]-phenyl}glycinate

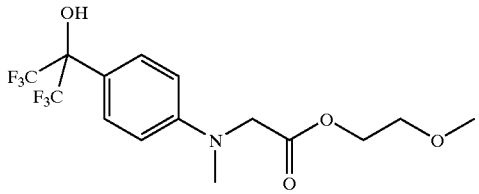

Prepared in the manner of Example 35 except 2-bromoethyl methyl ether was substituted for 4-chlorobenzyl chloride. Purification by reverse phase HPLC using a gradient elution of 60:40 H₂O/TFA:CH₃CN to 0:100 H₂O/TFA:CH₃CN at 254 nm afforded the title compound as a yellow oil (59%).

¹H NMR (CDCl₃) δ 7.45 (d, 2H), 6.67 (d, 2H), 4.22 (dt, 2H), 4.07 (s, 2H), 3.51 (dt, 2H), 3.27 (s, 3H), 3.05 (s, 3H). MS (ES+) m/z 390 (MH⁺). Anal. Calc. for C₁₅H₁₇NO₄F₆: C, 45.56; H, 4.30; N, 3.50. Found: C, 45.83; H, 4.68; N, 3.53. HRMS (MH⁺) Calc.: 390.1142. Found: 390.1146.

EXAMPLE 38

N²-Methyl-N¹,N¹-bis[4-(N-methyl-N-{4-[2,2,2-trifluoro-1-hydroxy-1-(trifluoromethyl)ethyl]phenyl}glycyl)morpholin-3-yl]-N²-{4-[2,2,2-trifluoro-1-hydroxy-1-(trifluoromethyl)ethyl]phenyl}glycinamide

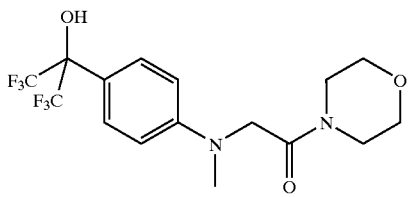

Prepared in the manner of Example 26 except N-methyl-N-{4-[2,2,2-trifluoro-1-hydroxy-1-(trifluoromethyl)ethyl]phenyl}glycine was substituted for N-{4-[2,2,2-trifluoro-1-hydroxy-1-(trifluoromethyl)ethyl]phenyl}alanine and morpholine was substituted for benzyl amine. Purification by reverse phase HPLC using a gradient elution of 60:40 H₂O/TFA:CH₃CN to 0:100 H₂O/TFA:CH₃CN at 254 nm afforded the title compound as a white solid (46%): mp=149° C. ¹H NMR (DMSO-d₆) δ 7.38 (d, 2H), 6.68 (d, 2H), 4.30 (s, 2H), 3.64 (m, 2H), 3.56 (m, 2H), 3.48 (m, 2H), 3.40 (m, 2H), 2.95 (s, 3H)). ¹³C NMR (DMSO-d₆) δ 167.4, 150.5, 127.4, 116.8, 111.4, 66.1, 52.4, 39.0. MS (ES+) m/z401 (MH⁺). HRMS (MH⁺) Calc.: 401.1313. Found: 401.1309.

EXAMPLE 39

N²-Methyl-N¹,N¹-bis[1-(N-methyl-N-{4-[2,2,2-trifluoro-1-hydroxy-1-(trifluoromethyl)ethyl]phenyl}glycyl)pyrrolidin-2-yl]-N²-{4-[2,2,2-trifluoro-1-hydroxy-1-(trifluoromethyl)ethyl]phenyl}glycinamide

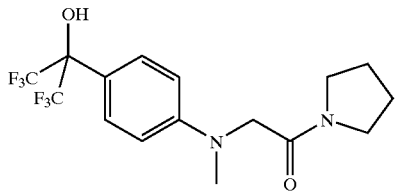

Prepared in the manner of Example 26 except N-methyl-N-{4-[2,2,2-trifluoro-1-hydroxy-1-(trifluoromethyl)ethyl]phenyl}glycine was substituted for N-{4-[2,2,2-trifluoro-1-hydroxy-1-(trifluoromethyl)ethyl]phenyl}alanine and pyrrolidine was substituted for benzyl amine. Purification by reverse phase HPLC using a gradient elution of 60:40 $H_2O$/TFA:$CH_3CN$ to 0:100 $H_2O$/TFA:$CH_3CN$ at 254 nm afforded the title compound as a white solid (33%): mp=184° C. ¹H NMR (DMSO-$d_6$) δ 8.25 (s, 1H), 7.38 (d, 2H), 6.68 (d, 2H), 4.18 (s, 2H), 3.46 (t, 2H), 3.28 (t, 2H), 2.97 (s, 3H), 1.92 (dt, 2H), 1.76 (dt, 2H). Anal. Calc. for $C_{16}H_{18}N_2O_2F_6$: C, 50.00; H, 4.72; N, 7.29. Found: C, 49.84; H, 4.95; N, 7.24. HRMS (MH⁺) Calc.: 385.1364. Found: 385.1367.

EXAMPLE 40

Ethyl N-(2,4-dichlorobenzyl)-N-{4-[2,2,2-trifluoro-1-hydroxy-1-(trifluoromethyl)ethyl]phenyl}glycinate

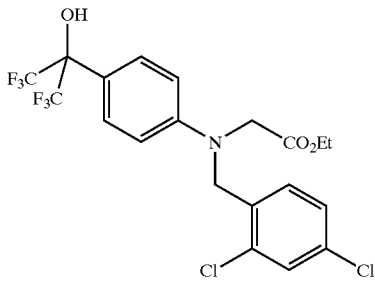

Step 1
2-{4-[(2,4-Dichlorobenzyl)amino]phenyl}-1,1,1,3,3,3-hexafluoropropan-2-ol A solution of 2-(4-aminophenyl)-1,1,1,3,3,3-hexafluoropropan-2-ol (Oakwoood, 1 g, 3.9 mmol) and 2,4-dichlorobenzaldehyde in methanol (21 mL) was stirred at ambient temperature. After 18 hours, glacial acetic acid (0.24 mL, 4.25 mmol) and sodium cyanoborohydride (388 mg, 4.25 mmol) were added. After stirring an additional 18 hours, the mixture was concentrated in vacuo and the residue dissolved in EtOAc. The organic layer was washed several times with brine, dried ($Na_2SO_4$), filtered, and concentrated. Purification by flash chromatography (4:1 hexanes/EtOAc) afforded the title compound as a white waxy solid (1.6 g, 99%). MS (ES+) m/z 418 (M⁺), 420 (M+2).
Step 2
Ethyl N-(2,4-dichlorobenzyl)-N-{4-[2,2,2-trifluoro-1-hydroxy-1-(trifluoromethyl)ethyl]phenyl}glycinate
Prepared in the manner of Example 5 steps 2–4 except 2-{4-[(2,4-dichlorobenzyl)amino]phenyl}-1,1,1,3,3,3-hexafluoropropan-2-ol was substituted for 1,1,1,3,3,3-hexafluoro-2-{4-[(2,2,2-trifluoroethyl)amino]phenyl}propan-2-ol. Purification by reverse phase HPLC using a gradient elution of 60:40 $H_2O$/TFA:$CH_3CN$ to 0:100 $H_2O$/TFA:$CH_3CN$ at 254 nm afforded the title compound as a white solid (58%): mp=111° C.
¹H NMR (CDCl₃) δ 7.60 (d, 2H), 7.52 (d, 1H), 7.31 (m, 2H), 6.68 (d, 2H), 4.77 (s, 2H), 4.34 (q, 2H), 4.21 (s, 2H), 1.37 (t, 3H). MS (ES+) m/z 504 (M⁺), 506 (M+2). Anal. Calc. for $C_{20}H_{17}NO_3\ Cl_2F_6$: C, 47.64; H, 3.40; N, 2.78. Found: C, 47.35; H, 3.57; N, 2.73. HRMS (M⁺) Calc.: 504.0581. Found: 504.0582.

EXAMPLE 41

Ethyl N-(3-chlorobenzyl)-N-{4-[2,2,2-trifluoro-1-hydroxy-1-(trifluoromethyl)ethyl]phenyl}glycinate

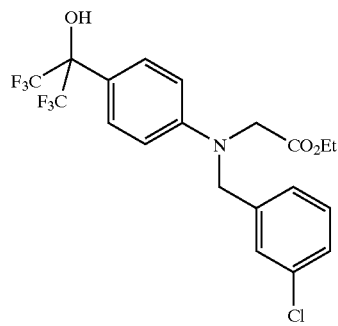

Prepared in the manner of Example 40 except 3-chlorobenzaldehyde was substituted for 2,4-dichlorobenzaldehyde. Purification by reverse phase HPLC using a gradient elution of 60:40 $H_2O$/TFA:$CH_3CN$ to 0:100 $H_2O$/TFA:$CH_3CN$ at 254 nm afforded the title compound as a white solid (68%): mp=81.5° C. ¹H NMR (CDCl₃) δ 7.38 (d, 2H), 7.15 (m, 3H), 7.04 (m, 1H), 6.55 (d, 2H), 4.51 (s, 2H), 4.09 (q, 2H), 3.97 (s, 2H), 1.17 (t, 3H). MS (ES+) m/z 470 (MH⁺). Anal. Calc. for $C_{20}H_{18}NO_3\ ClF_6$: C, 51.13; H, 3.86; N, 2.98. Found: C, 50.95; H, 4.05; N,2.99. HRMS (MH⁺) Calc.: 470.0980. Found: 470.0976.

EXAMPLE 42

Ethyl N-(4-ethoxybenzyl)-N-{4-[2,2,2-trifluoro-1-hydroxy-1-(trifluoromethyl)ethyl]phenyl}glycinate

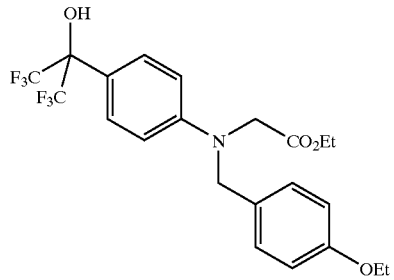

Prepared in the manner of Example 40 except 4-ethoxybenzaldehyde was substituted for 2,4-dichlorobenzaldehyde. Purification by reverse phase HPLC using a gradient elution of 60:40 $H_2O$/TFA:$CH_3CN$ to 0:100 $H_2O$/TFA:$CH_3CN$ at 254 nm afforded the title compound as a colorless oil (79%). ¹H NMR (CDCl₃) δ 7.51 (d, 2H), 7.20

(d, 2H), 6.88 (dd, 2H), 6.77 (dd, 2H), 4.62 (s, 2H), 4.22 (q, 2H), 4.08 (s, 2H), 4.04 (q, 2H), 1.43 (t, 3H), 1.28 (t, 3H). MS (ES+) m/z 502 (M$^+$Na). Anal. Calc. for $C_{22}H_{23}NO_4F_6$: C, 55.12; H, 4.84; N, 2.92. Found: C, 54.92; H, 4.90; N, 2.93. HRMS (M+Na) Calc.: 502.1446. Found: 502.1448.

EXAMPLE 43

Ethyl N-(4-methoxybenzyl)-N-{4-[2,2,2-trifluoro-1-hydroxy-1-(trifluoromethyl)ethyl]phenyl}glycinate

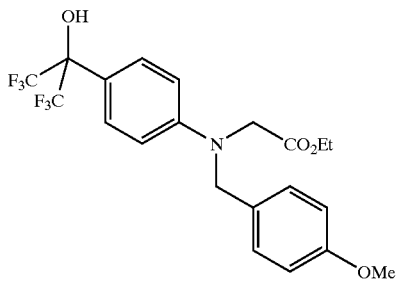

Prepared in the manner of Example 40 except 4-methoxybenzaldehyde was substituted for 2,4-dichlorobenzaldehyde. Purification by reverse phase HPLC using a gradient elution of 60:40 H$_2$O/TFA:CH$_3$CN to 0:100 H$_2$O/TFA:CH$_3$CN at 254 nm afforded the title compound as a white solid (67%): mp=68° C. $^1$H NMR (CDCl$_3$) δ 7.51 (d, 2H), 7.21 (d, 2H), 6.90 (dd, 2H), 6.77 (dd, 2H), 4.62 (s, 2H), 4.24 (q, 2H), 4.10 (s, 2H), 3.82 (s, 3H), 1.28 (t, 3H). MS (ES+) m/z 488 (M+Na). Anal. Calc. for $C_{21}H_{21}NO_4F_6$: C, 54.20; H, 4.55; N, 3.01. Found: C, 54.03; H, 4.65; N, 3.04. HRMS (M+Na) Calc.: 488.1289. Found: 488.1289.

EXAMPLE 44

Ethyl 1-benzyl-4-({4-[2,2,2-trifluoro-1-hydroxy-1-(trifluoromethyl)ethyl]}amino)piperidine-4-carboxylate trifluoroacetate

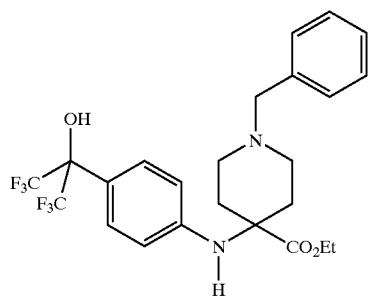

Step 1
1-Benzyl-4-({4-[2,2,2-trifluoro-1-hydroxy-1-(trifluoromethyl)ethyl]phenyl-}amino)piperidine-4-carbonitrile To a stirred solution of 1-benzyl-4-piperidone (1.3 mL, 7.0 mmol) and 2-(4-aminophenyl)-1,1,1,3,3,3-hexafluoropropan-2-ol (Oakwood, 2.0 g, 7.7 mmol) in glacial acetic acid (6.6 mL) was added trimethylsilyl cyanide (0.9 mL, 7.0 mmol) over 5 minutes. After 30 minutes, the reaction was poured in to a mixture of ice (6.5 g) and NH$_4$OH (6.5 mL). Additional NH$_4$OH was added until pH=10. The product was extracted with CH$_2$Cl$_2$ (3×), then washed with brine, dried (Na$_2$SO$_4$), and concentrated to afford the title compound as an off-white solid (3.4 g, quantitative yield). MS (ES+) m/z 458 (MH$^+$).

Step 2

1-Benzyl-4-({4-[2,2,2-trifluoro-1-hydroxy-1-(trifluoromethyl)ethyl]phenyl}amino)-piperidine-4-carboxylic acid The product from step 1 (1.0 g, 2.19 mmol) was dissolved in 3M NaOH (16.2 mL) and H$_2$O$_2$ added (5.7 mL, 30 wt. %). The reaction mixture was warmed at 90° C. for 18 hours. The reaction mixture was cooled to ambient temperature and washed with EtOAc. The aqueous layer was cooled to 0° C. and 6N HCl added until pH=4. The product was extracted with EtOAc (3×) and the combined organics washed with brine, dried (Na$_2$SO$_4$), and concentrated. Purification by reverse phase HPLC using a gradient elution of 80:20 H$_2$O/TFA:CH$_3$CN to 20:80 H$_2$O/TFA:CH$_3$CN at 254 nm afforded the title compound as a white solid (500 mg, 48%). MS (ES+) m/z 477 (MH$^+$).

Step 3

Prepared in the manner of Example 5 step 4 except 1-benzyl-4-({4-[2,2,2-trifluoro-1-hydroxy-1-(trifluoromethyl)ethyl]phenyl}amino)-piperidine-4carboxylic acid was substituted for N-(2,2,2-trifluoroethyl)-N-{4-[2,2,2-trifluoro-1-hydroxy-1-(trifluoromethyl)-ethyl]phenyl}glycine. Purification by reverse phase HPLC using a gradient elution of 90:10 H$_2$O/TFA:CH$_3$CN to 50:50 H$_2$O/TFA:CH$_3$CN at 254 nm afforded the title compound as an off-white solid (50 mg, 30%). $^1$H NMR (mixture of rotomers, DMSO-d$_6$) δ 9.63 (br s, 1H), 8.32 (s, 1H), 750 (m, 5H), 7.37 (d, 2H), 6.58 (d, 2H), 4.36 (d, 2H), 4.10 (q, 2H), 3.32 (m, 2H), 3.18 (m, 2H), 2.33 (m, 2H), 2.19 (m, 2H), 1.04 (t, 3H). MS (ES+) m/z 505 (MH$^+$). Anal. Calc. for $C_{24}H_{26}N_2O_3F_6$+1.4 TFA+1 H$_2$O: C, 47.19; H, 4.34; N, 4.11. Found: C, 47.40; H, 4.61; N, 3.86. HRMS (MH$^+$) Calc.: 505.1926. Found: 505.1942.

EXAMPLE 45

Ethyl 4-({4-[2,2,2-trifluoro-1-hydroxy-1-(trifluoromethyl)ethyl]phenyl}amino)-tetrahydro-2H-pyran-4-carboxylate

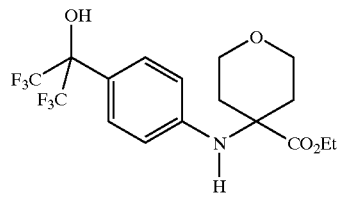

Prepared in the manner of Example 44 except tetrahydro-4H-pyran-4-one was substituted for 1-benzyl-4-piperidone. No purification was necessary. Product obtained as a light yellow solid (92%). $^1$H NMR (DMSO-d$_6$) δ 8.27 (s, 1H), 7.33 (d, 2H), 6.58 (d, 2H), 6.43 (s, 1H), 4.09 (q, 2H), 3.65 (m, 4H), 2.05 (m, 4H), 1.06 (t, 3H). MS (ES+) m/z 416 (MH$^+$). Anal. Calc. for $C_{17}H_{19}O_4F_6$: C, 49.16; H, 4.61; N, 3.37. Found: C, 49.03; H, 4.92; N, 3.11. HRMS (MH$^+$) Calc.: 416.1297. Found: 416.1297.

EXAMPLE 46

Ethyl 4-({4-[2,2,2-trifluoro-1-hydroxy-1-(trifluoromethyl)ethyl]phenyl}-amino)tetrahydro-2H-thiopyran-4-carboxylate 1,1-dioxide trifluoroacetate

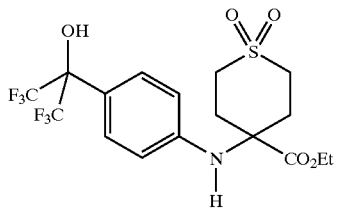

Prepared in the manner of Example 44 except tetrahydrothiopyran-4-one was substituted for 1-benzyl-4-piperidone. No purification was necessary. Product obtained as a light yellow solid (92%). $^1$H NMR (DMSO-d$_6$) δ 8.32 (s, 1H), 7.38 (d, 2H), 6.63 (d, 2H), 6.54 (s, 1H), 4.12 (q, 2H), 3.22 (m, 2H), 3.12 (m, 2H), 2.50 (m, 2H), 2.40 (m, 2H), 1.08 (t, 3H). MS (ES+) m/z 464 (MH$^+$). Anal. Calc. for $C_{17}H_{19}NSO_5F_6$+0.1H$_2$O: C, 43.89; H, 4.16; N, 3.01. Found: C, 44.12; H, 4.52; N, 2.61. HRMS (MH$^+$) Calc.: 464.0966. Found: 464.0969.

EXAMPLE 47

1-(Benzyl{4-[2,2,2-trifluoro-1-hydroxy-1-(trifluoromethyl)ethyl]phenyl}amino)-pentan-2-ol

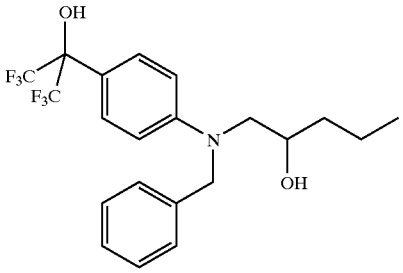

Prepared in the manner of Example 34 except 1-(benzyl{4-[2,2,2-trifluoro-1-hydroxy-1-(trifluoromethyl)ethyl]phenyl}amino)pentan-2-one was substituted for 1-(methyl{4-[2,2,2-trifluoro-1-hydroxy-1-(trifluoromethyl)ethyl]phenyl}amino)-pentan-2-one. Purification by reverse phase HPLC using a gradient elution of 60:40 H$_2$O/TFA:CH$_3$CN to 0:100 H$_2$O/TFA:CH$_3$CN at 254 nm afforded the title compound as an yellow waxy solid (34%). $^1$H NMR (CDCl$_3$) δ 7.48 (d, 2H), 7.33 (t, 2H), 7.27 (m, 1H), 7.20 (d, 2H), 6.81 (d, 2H), 4.70 (s, 2H), 4.03 (m, 1H), 3.56 (dd, 1H), 3.41 (dd, 1H), 1.50 (m, 4H), 0.97 (t, 3H). Anal. Calc. for $C_{21}H_{23}NO_2F_6$+0.1 TFA+0.5 H$_2$O: C, 55.64; H, 5.35; N, 3.06. Found: C, 55.71; H, 5.56; N, 2.73. HRMS (MH$^+$). Calc.: 436.1711. Found: 436.1728.

EXAMPLE 48

1-((2,2,2-Trifluoroethyl){4-[2,2,2-trifluoro-1-hydroxy-1-(trifluoromethyl)ethyl]phenyl}amino)pentan-2-ol

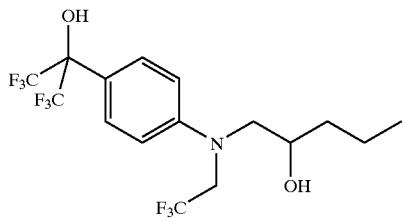

Prepared in the manner of Example 34 except 1-((2,2,2-trifluoroethyl){4-[2,2,2-trifluoro-1-hydroxy-1-(trifluoromethyl)ethyl]phenyl}amino)pentan-2-one was substituted for 1-(methyl{4-[2,2,2-trifluoro-1-hydroxy-1-(trifluoromethyl)ethyl]-phenyl}amino)-pentan-2-one. Purification by reverse phase HPLC using a gradient elution of 80:20 H$_2$O/TFA:CH$_3$CN to 50:50 H$_2$O/TFA:CH$_3$CN at 254 nm afforded the title compound as white solid (71%). $^1$H NMR (CDCl$_3$) δ 7.48 (d, 2H), 6.77 (d, 2H), 4.05 (q, 2H), 3.98 (m, 1H), 3.53 (dd, 1H), 3.13 (dd, 1H), 1.42 (m, 4H), 3H). Anal. Calc. for $C_{16}H_{18}NO_2F_9$: C, 44.97; H, 4.25; N, 3.28. Found: C, 44.77; H, 4.49; N, 3.19. HRMS (MH$^+$). Calc.: 428.1272. Found: 428.1289.

EXAMPLE 49

Ethyl 4-tert-butyl-1-({4-[2,2,2-trifluoro-1-hydroxy-1-(trifluoromethyl)ethyl]phenyl}amino)cyclohexanecarboxylate

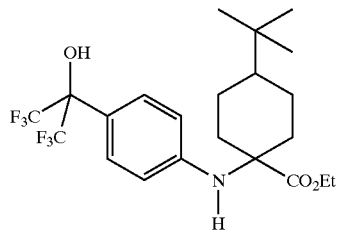

Prepared in the manner of Example 9 except 4-tert-butylcyclohexanone was substituted for phenylacetaldehyde. Purification by flash chromatography (5:1 hexanes/EtOAc) afforded the title compound as a white solid (26%): mp=107° C. $^1$H NMR (CDCl$_3$) δ 7.34 (d, 2H), 6.48 (d, 2H), 4.07 (q, 2H), 2.16 (m, 2H), 1.76 (m, 2H), 1.60 (m, 2H), 1.21 (m, 2H), 1.03 (t, 3H), 0.78 (s, 9H). Anal. Calc. for $C_{22}H_{29}NO_3F_6$: C, 56.29; H, 6.23; N, 2.98. Found: C, 56.03; H, 6.58; N, 2.84. HRMS (MH$^+$). Calc.: 470.2130, found. Found: 470.2145.

EXAMPLE 50

Ehyl 4-methyl-1-({4-[2,2,2-trifluoro-1-hydroxy-1-(trifluoromethyl)ethyl]phenyl}amino)cyclohexanecarboxylate

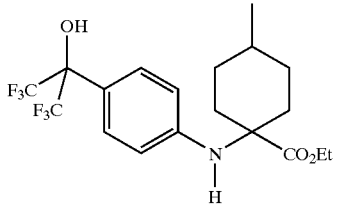

Prepared in the manner of Example 9 except 4-methylcyclohexanone was substituted for phenylacetaldehyde. Purification by flash chromatography (8:1 hexanes/EtOAc) afforded the title compound as a yellow solid (38%): mp=142.6° C. $^1$H NMR (CDCl$_3$) δ 7.33 (d, 2H), 6.48 (d, 2H), 4.07 (t, 2H), 2.10 (m, 2H), 1.78 (m, 2H), 1.52 (m, 3H), 1.15 (m, 2H), 1.03 (t, 3H), 0.85 (d, 3H). Anal. Calc. for C$_{19}$H$_{23}$NO$_3$F$_6$: C, 53.40; H, 5.42; N, 3.28. Found: C, 53.29; H, 5.50; N, 3.18. HRMS (MH$^+$). Calc.: 426.1504. Found: 426.1518.

EXAMPLE 51

Ethyl 1-{4-[2,2,2-trifluoro-1-hydroxy-1-(trifluoromethyl)ethyl]phenyl}-D-prolinate

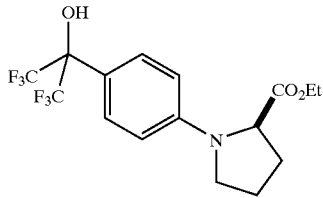

Prepared in the manner of Example 4 except D-proline ethyl ester was substituted for ethyl pipecolinate. Purification by flash chromatography (6:1 hexanes/EtOAc) afforded the title compound as a yellow oil (23%). $^1$H NMR (DMSO-d$_6$) δ 8.31 (s, 1H), 7.72 (d, 2H), 6.55 (d, 2H), 4.31 (m, 1H), 4.11 (m, 2H), 3.46 (m, 1H), 2.27 (m, 1H), 2.02 (m, 4H), 1.17 (t, 3H). Anal. Calc. for C$_{16}$H$_{17}$NO$_3$F$_6$: C, 49.88; H, 4.45; N, 3.64. Found: C, 49.74; H, 4.72; N, 3.49. HRMS (MH$^+$). Calc.: 386.1191. Found: 386.1206.

EXAMPLE 52

Ethyl 1-{4-[2,2,2-trifluoro-1-hydroxy-1-(trifluoromethyl)ethyl]phenyl}-L-prolinate

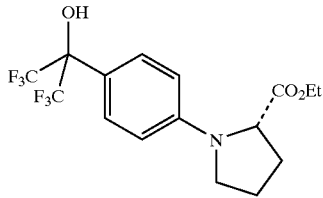

Prepared in the manner of Example 4 except L-proline ethyl ester was substituted for ethyl pipecolinate. Purification by flash chromatography (6:1 hexanes/EtOAc) afforded the title compound as a yellow oil (32%). $^1$H NMR (DMSO-d$_6$) δ 8.30 (s, 1H), 7.42 (d, 2H), 6.55 (d, 2H), 4.31 (m, 1H), 4.11 (m, 2H), 3.46 (m, 1H), 2.27 (m, 1H), 2.06 (m, 4H), 1.17 (t, 3H). Anal. Calc. for C$_{16}$H$_{17}$NO$_3$F$_6$+0.3H$_2$O: C, 49.19; H, 4.54; N, 3.59. Found: C, 49.19; H, 4.60; N, 3.56. HRMS (MH$^+$). Calc.: 386.1191. Found: 386.1202.

EXAMPLE 53

Ethyl N-{4-[2,2,2-trifluoro-1-hydroxy-1-(trifluoromethyl)ethyl]phenyl}-N-[4-(trifluoromethyl)benzyl]glycinate

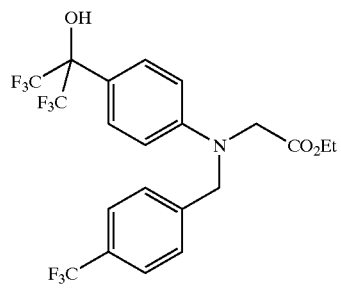

Prepared in the manner of Example 16 except 4-(trifluoromethyl)benzyl bromide was substituted for 4-chlorobenyl chloride. Purification by flash chromatography (10:1 to 5:1 hexanes/EtOAc) afforded the title compound as a yellow oil (30%). $^1$H NMR (CDCl$_3$) δ 7.62 (d, 2H), 7.52 (d, 2H), 7.43 (d, 2H), 6.68 (d, 2H), 4.73 (s, 2H), 4.25 (q, 2H), 4.14 (s, 2H), 1.30 (t, 3H). Anal. Calc. for C$_{21}$H$_{18}$NO$_3$F$_9$: C, 50.11; H, 3.60; N, 2.78. Found: C, 50.01; H, 3.98; N, 2.61. HRMS (MH$^+$). Calc.: 504.1221. Found: 504.1227.

EXAMPLE 54

LXR Reporter Gene Transactivation Assay

Human hepatic cells (Huh-7) were cotransfected with a luciferase reporter gene (pGal4-RE), where transcription of luciferase gene is driven by the Gal4 response element, and a chimeric gene construct of liver X receptor (Gal4$_{DBD}$-LXRα$_{LBD}$), which comprises a DNA sequence that encodes a hybrid protein of LXR ligand binding domain (LXR$_{LBD}$) and Gal4 DNA-binding domain (Gal4$_{DBD}$). The transfection was performed in culture dishes using LipofectAMINE2000 reagent. The transfected cells were harvested 20 hr later and resuspended in assay medium containing RPMI 1640 medium, 2% fetal bovine lipoprotein deficient serum, 100 units/ml pencillin and 100 µg/ml streptomycin.

In screening for LXR agonists, the transfected cells were dispensed in an assay plate (384-well white tissue culture plate) containing the test compounds at 10 µM final concentration and incubated for 24 hr. The effects of test compounds on the activation of LXR$_{LBD}$ and hence luciferase transcription was determined by measuring the luciferase activity using Steady-Glo luciferase assay substrate. Luciferase activity results are expressed as the fold-induction relative to DMSO controls. Compounds that exhibited >10 fold induction were then retested and the EC$_{50}$ was determined as the concentration necessary to produce 50% of the maximal luciferase activity. Each of the compounds of Examples 1–53 was found to have an EC$_{50}$ of less than 50 µM.

What is claimed is:

1. A compound of Formula I:

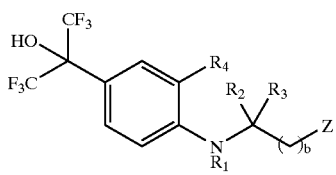

(Formula I)

wherein:

b is 0–3;

R₁ is hydrogen, acyl, or optionally substituted alkyl, heterocyclo, or aralkyl;

R₂ and R₃ are independently hydrogen or optionally substituted alkyl, aryl, heteroaryl, aminoalkyl, hydroxyalkyl, or thioalkyl; one of R₂ and R₃, or R₂ and R₃ together with the atom to which they are attached may form a carbocyclic or heterocyclic ring;

R₄ is hydrogen or together with R₁ and the atoms to which they are attached form a heterocyclic ring;

Z is —CO₂Z₁, —CH₂NZ₁Z₂, —C(O)Z₁, —CH(OH)Z₁, —CH₂OZ₁, —CH₂OC(O)Z₁, or —C(O)NZ₁Z₂, and Z₁ and Z₂ are independently hydrogen or optionally substituted alkyl, heterocyclo, or aralkyl;

provided, however, when R₁ is hydrogen and one of R₂ and R₃ is hydrogen, the other of R₂ and R₃ is not hydrogen or methyl.

2. The compound of claim 1 wherein R₁ is a substituted or unsubstituted benzyl group.

3. The compound of claim 1 wherein R₁ is a substituted or unsubstituted benzoyl group.

4. The compound of claim 1 wherein Z is —CO₂H.

5. The compound of claim 1 wherein Z is —C(O)NZ₁Z₂ and Z₁ and Z₂ are as defined in claim 1.

6. The compound of of claim 1 wherein Z is —CO₂Z₁ and Z₁ is as defined in claim 1.

7. The compound of claim 1 wherein Z is —CH(OH)Z₁ and Z₁ is as defined in claim 1.

8. A compound selected from compounds of the group consisting of

Ethyl N-methyl-N-{4-[2,2,2-trifluoro-1-hydroxy-1-(trifluoromethyl)ethyl]-phenyl}alaninate;

Ethyl 2-methyl-N-{4-[2,2,2-trifluoro-1-hydroxy-1-(trifluoromethyl)ethyl]phenyl}alaninate;

Ethyl N-(2,2,2-trifluoroethyl)-N-{4-[2,2,2-trifluoro-1-hydroxy-1-(trifluoromethyl)ethyl]phenyl}glycinate;

Ethyl N-ethyl-N-{4-[2,2,2-trifluoro-1-hydroxy-1-(trifluoromethyl)ethyl]-phenyl}glycinate;

Ethyl N-methyl-N-{4-[2,2,2-trifluoro-1-hydroxy-1-(trifluoromethyl)ethyl]-phenyl}glycinate;

Methyl phenyl({4-[2,2,2-trifluoro-1-hydroxy-1-(trifluoromethyl)ethyl]-phenyl}amino)acetate hydrochloride;

Methyl N-{4-[2,2,2-trifluoro-1-hydroxy-1-(trifluoromethyl)ethyl]phenyl}-phenylalaninate;

Methyl (4-chlorophenyl)({4-[2,2,2-trifluoro-1-hydroxy-1-(trifluoromethyl)-ethyl]phenyl}amino)acetate;

Methyl (3,4-dichlorophenyl)({4-[2,2,2-trifluoro-1-hydroxy-1-(trifluoromethyl)-ethyl]phenyl}amino) acetate;

Ethyl 3-({4-[2,2,2-trifluoro-1-hydroxy-1-(trifluoromethyl)ethyl]phenyl}amino)-butanoate;

Ethyl N-methyl-N-{4-[2,2,2-trifluoro-1-hydroxy-1-(trifluoromethyl)ethyl]-phenyl}-beta-alaninate;

Ethyl N-(4-chlorobenzyl)-N-{4-[2,2,2-trifluoro-1-hydroxy-1-(trifluoromethyl)-ethyl]-phenyl}glycinate;

Ethyl N-(3,4-dichlorobenzyl)-N-{4-[2,2,2-trifluoro-1-hydroxy-1-(trifluoromethyl)ethyl]phenyl}glycinate;

Ethyl N-(4-methylbenzyl)-N-{4-[2,2,2-trifluoro-1-hydroxy-1-(trifluoromethyl)-ethyl]phenyl}glycinate;

Ethyl N-benzyl-N-{4-[2,2,2-trifluoro-1-hydroxy-1-(trifluoromethyl)ethyl]-phenyl}glycinate;

N-Methyl-N-{4-[2,2,2-trifluoro-1-hydroxy-1-(trifluoromethyl)ethyl]phenyl}-glycine;

1,1,1,3,3,3-Hexafluoro-2-{4-[(2-hydroxyethyl)(methyl)amino]phenyl}-propan-2-ol;

2-(Methyl-{4-[2,2,2-trifluoro-1-hydroxy-1-(trifluoromethyl)ethyl]phenyl}-amino)propan-1-ol;

N-1-Benzyl-N-2-{4-[2,2,2-trifluoro-1-hydroxy-1-(trifluoromethyl)ethyl]-phenyl}alaninamide;

N-1-Benzyl-N-2-methyl-N-2-{4-[2,2,2-trifluoro-1-hydroxy-1-(trifluoromethyl)-ethyl]phenyl}glycinamide;

N-1-Benzyl-N-3-methyl-N-3-{4-[2,2,2-trifluoro-1-hydroxy-1-(trifluoromethyl)-ethyl]phenyl}-beta-alaninamide;

N-1-Methoxy-N-1-N-2-dimethyl-N-2-{4-[2,2,2-trifluoro-1-hydroxy-1-(trifluoro-methyl)ethyl]phenyl}glycinamide;

1-(Methyl{4-[2,2,2-trifluoro-1-hydroxy-1-(trifluoromethyl)ethyl]phenyl}-amino)pentan-2-one;

1-(Methyl{4-[2,2,2-trifluoro-1-hydroxy-1-(trifluoromethyl)ethyl]phenyl}-amino)pentan-2-ol;

4-Chlorobenzyl N-methyl-N-{4-[2,2,2-trifluoro-1-hydroxy-1-(trifluoromethyl)-ethyl]phenyl}glycinate;

2-Ethoxyethyl N-methyl-N-{4-[2,2,2-trifluoro-1-hydroxy-1-(trifluoromethyl)-ethyl]-phenyl}glycinate;

2-Methoxyethyl N-methyl-N-{4-[2,2,2-trifluoro-1-hydroxy-1-(trifluoromethyl)-ethyl]-phenyl}glycinate;

N²-Methyl-N¹,N¹-bis[4-(N-methyl-N-{4-[2,2,2-trifluoro-1-hydroxy-1-(trifluoromethyl)ethyl]phenyl}glycyl)morpholin-3-yl]-N²-{4-[2,2,2-trifluoro-1-hydroxy-1-(trifluoromethyl)ethyl]phenyl}glycinamide;

N²-Methyl-N¹,N¹-bis[1-(N-methyl-N-{4-[2,2,2-trifluoro-1-hydroxy-1-(trifluoromethyl)ethyl]phenyl}glycyl)pyrrolidin-2-yl]-N²-{4-[2,2,2-trifluoro-1-hydroxy-1-(trifluoromethyl)ethyl]phenyl}glycinamide;

Ethyl N-(2,4-dichlorobenzyl)-N-{4-[2,2,2-trifluoro-1-hydroxy-1-(trifluoromethyl)ethyl]phenyl}glycinate;

Ethyl N-(3-chlorobenzyl)-N-{4-[2,2,2-trifluoro-1-hydroxy-1-(trifluoromethyl)ethyl]phenyl}glycinate;

Ethyl N-(4-ethoxybenzyl)-N-{4-[2,2,2-trifluoro-1-hydroxy-1-(trifluoromethyl)ethyl]phenyl}glycinate;

Ethyl N-(4-methoxybenzyl)-N-{4-[2,2,2-trifluoro-1-hydroxy-1-(trifluoromethyl)ethyl]phenyl}glycinate;

1-(Benzyl{4-[2,2,2-trifluoro-1-hydroxy-1-(trifluoromethyl)ethyl]phenyl}amino)-pentan-2-ol;

1-((2,2,2-Trifluoroethyl){4-[2,2,2-trifluoro-1-hydroxy-1-(trifluoromethyl)ethyl]phenyl}amino)pentan-2-ol;

Ethyl N-{4-[2,2,2-trifluoro-1-hydroxy-1-(trifluoromethyl)ethyl]phenyl}-N-[4-(trifluoromethyl)benzyl]glycinate;

Ethyl N-(pyridin-3-ylmethyl)-N-{4-[2,2,2-trifluoro-1-hydroxy-1-(trifluoromethyl)ethyl]phenyl}glycinate;

Ethyl N-(2-chlorobenzyl)-N-{4-[2,2,2-trifluoro-1-hydroxy-1-(trifluoromethyl)ethyl]phenyl}glycinate;

Ethyl N-(2-methoxyethyl)-N-{4-[2,2,2-trifluoro-1-hydroxy-1-(trifluoromethyl)ethyl]phenyl}glycinate;

2-{4-[(2-Ethoxyethyl)(methyl)amino]phenyl}-1,1,1,3,3,3-hexafluoro-propan-2-ol;

2-(Methyl{4-[2,2,2-trifluoro-1-hydroxy-1-(trifluoromethyl)ethyl]phenyl}amino)ethyl propionate;

Methyl (4-methylphenyl)({4-[2,2,2-trifluoro-1-hydroxy-1-(trifluoromethyl)ethyl]-phenyl}amino)acetate.

9. A method for treating conditions regulated by the liver X-receptor in a mammal in need of such treatment comprising administering an effective liver X-receptor modulating amount of a compound according to claim 1.

10. A method according to claim 9 wherein the condition treated is atherosclerosis.

11. A method according to claim 9 wherein the condition treated is dyslipidemia.

12. A method according to claim 9 wherein the condition treated is diabetes.

13. A method according to claim 9 wherein the condition treated is Alzheimers disease.

14. A method according to claim 9 wherein the condition treated is Niemann-Pick disease.

* * * * *